United States Patent [19]
Wigler et al.

[11] Patent Number: 6,080,540
[45] Date of Patent: Jun. 27, 2000

[54] CLONING OF MAMMALIAN GENES IN MICROBIAL ORGANISMS AND METHODS FOR PHARMACOLOGICAL SCREENING

[75] Inventors: Michael H. Wigler, Lloyd Harbor; John J. Colicelli, Huntington, both of N.Y.

[73] Assignee: Cold Spring Harbor Laboratory, Cold Spring, N.Y.

[21] Appl. No.: 07/511,715

[22] Filed: Apr. 20, 1990

[51] Int. Cl.[7] .................................. C12Q 1/68; C12N 1/19
[52] U.S. Cl. .................................. 435/6; 435/7.1; 435/29; 435/252.3; 435/254.2; 435/254.21
[58] Field of Search .................................. 435/172.1, 69.2, 435/6, 7.1, 29, 252.3, 254.2, 254.21; 536/27

[56] References Cited

PUBLICATIONS

Dietzel et al., Cell, vol. 50, pp. 1001–1007, 1987.
Xiong et al., Cell, vol. 65, pp. 691–699, 1991.
Hosaka et al., FEBS Letters, vol. 304, pp. 229–232, 1992.
Chang, A.C.Y. et al., *Nature*, 275: 617–624 (1978).
Goddard, J.M. et al., *Proc. Natl. Acad. Sci. USA*, 80: 4281–4285 (1983).
Yeung, C.–Y. et al., *J. Biol. Chem.* 260: 10,299,10,307 (1985).
McKnight, G.L. and G.L. McConaughy, *Proc. Natl. Acad. Sci. USA*, 80: 4412–4416 (1983).
Kataoka, T. et al., *Cell*, 43: 493–505 (1985).
Kataoka, T., et al., *Cell*, 40: 19–26 (1985).
DeFeo–Jones, D. et al., *Science*, 228: 179–184 (1985).
Field, J. et al., *Mol. Cell. Biol.* 8: 2159–2165.
Sass, P. et al., *Proc. Natl. Acad. Sci. USA* 83: 9303–9307 (1986).
Nikawa, J.–I. et al., *Mol. Cell. Biol.*, 7: 3629–3636.
Wigler, M. et al., *Cold Spring Harbor Symp. Quant. Biol.*, 53: 649–655 (1988).
Powers, S. et al., *Mol. Cell. Bil.*, 9: 390–395 (Feb., 1989).
Field, J. et al., *Science*, 247: 464–467 (Jan. 1990).
Henikoff, S. et al., *Nature*, 289: 33–37 (1981).
Jacquet, M., et al., *J. Mol. Appl Genet.*, 1: 513–525 (1982).
Lee, M.G. and P. Nurse, *Nature*, 327: 31–35 (1987).
Metzger, D. et al., *Nature*, 334: 31–36 (1988).
Colicelli, J. et al., *Proc. Natl. Acda Sci. USA*, 86: 3599–3603 (May, 1989).
Swinnen, J. V. et al., *Proc. Natl. Acad. Sci. USA*, 86: 5325–5329 (Jul., 1989).
Ballester, R. et al., *Cell*, 59: 681–686 (Nov., 1989).
Camonis, J. et al., *Gene*, 86: 263–268 (1990).
Nakafuku, M. et al., *Proc. Natl Acad. Sci. USA*, 85: 1374–1378 (1988).
Hoshino, S.–I et al., *EMBO J.*, 8: 3807–3814 (Dec., 1989).
Altman, M. et al., *J. Biol. Chem.* 264: 12,145–12,147 (Jul., 1989).

*Primary Examiner*—David Guzo
*Attorney, Agent, or Firm*—Marshall, O'Toole, Gerstein, Murray & Borun

[57] ABSTRACT

A method of cloning mammalian genes encoding proteins which can function in microorganisms, particularly yeast, and can modify, complement, or suppress a genetic defect associated with an identifiable phenotypic alteration or characteristic in the microorganism. It further relates to mammalian genes cloned by the present method, as well as to products encoded by such genes and antibodies which can bind the encoded proteins. More specifically, the present invention relates to a method of cloning mammalian genes which encode products which modify, complement or suppress a genetic defect in a biochemical pathway in which cAMP participates or in a biochemical pathway which is controlled, directly or indirectly, by a RAS protein, to products (RNA, proteins) encoded by the mammalian genes cloned in this manner and to antibodies which can bind the encoded proteins.

10 Claims, 18 Drawing Sheets

DPD
1

CTTGCGAATCGTAAGAAACAATTTCACC

CTGCTGACAAACCTTCACGGAGCACCGAACAAGAGGTCGCCAGCGGCTAGTCAGGCTCCAGTCCACCAGAGTCAGCCTCAGCCTGCAAGAAGAATCATATCAGAAACTAGCA

ATGGAGACGCTGGAGGAACTAGACTGGTGCCTAGACCAGCCATCCAGAGACTTCAGCGAGATGGCTTCAAACAAGTTCAAAAGGATGCTG
METGluThrLeuGluGluLeuAspLeuAspTrpCysLeuAspGlnProSerLeuAspThrIleGlnThrIleGlnLysPheLysArgMETLeu

AACCCGGAGCTGACACACCTCTCAGAGATGAGCAGATCAGGGAACCAAGTGTCTGAATACATTCGAACACGTTCTTAGACAAGCAGAACGATGTGGAAATCCCA
AsnArgGluLeuThrHisLeuSerGluMETSerGluArgSerGlyAsnGlnValSerGluTyrIleSerAsnThrPheLeuAspLysGlnAsnAspValGluIlePro

TCTCCCACCCAGAAGGACAGGGAGAAGAAGAAGCACAGCTCATGACCCAGATAAGTGGAGTGAAGAAACTGATGCACACGTCAAGCCTGAACAACAACAAGC
SerProThrGlnLysAspArgGluLysLysLysLysGlnLeuMETThrGlnIleSerGlyValLysLysLeuMETHisSerSerLeuAsnAsnThrSer

ATCTCACGCTTTGGAGTCAACACGGAAAATGAGGATCATCTAGCCAAGGAGCTGGAAGACCTGAACAAATGGGCCTAACATCTTCAACGTTGGCTGGGTACTCC
IleSerArgPheGlyValAsnThrGluAsnGluAspHisLeuAlaLysGluLeuAspLeuAsnLysTrpGlyLeuAsnIlePheAsnValAlaGlyTyrSer

CATAAATCGGCCCCTCACATGCATCATGTACGCCATTTTCCAGGAAAGAGACCTTCTAAAGACGTTTAAAATCTCCTCCGACACCTTCGTAACCTACATGATGACT
HisAsnArgProLeuThrCysIleMETTyrAlaIlePheGlnGluArgAspLeuLeuLysThrPheLysIleSerSerAspThrPheValThrTyrMETMETThr

TTAGAAGACCATTACCATTCTGATGTGGCGTATCACAACAGCCTGCCCAGTCCAACGCACGTTCTCCTCCTCTACGCCAGCACTGGATGCT
LeuGluAspHisTyrHisSerAspValAlaTyrHisAsnSerLeuProSerProAlaLeuAspAla

GTCTTCACAGACCTGAAATCCTGGCTGCCATTTTGCAGCTGCCATCCATGATGTTGATCATCCTGGAGTCTCCAATCAGTTTCTCATCAATACAAATTCCGAA
ValPheThrAspLeuLysSerTrpLeuProPheAlaAlaAlaIleProGlyValSerAsnGlnPheLeuIleAsnThrAsnSerGlu

CTTGCTTTGATGTATAATGACGAATCTGTCTGGAAAACCTCCTCCAAGAGGAACATTGCGACATCTTTCAGAATCTTACC
LeuAlaLeuMETTyrAsnAspGluSerValLeuGluAsnHisHisLeuAlaValGlyPheLysLeuLeuGlnGluHisCysAspIlePheGlnAsnLeuThr

AAGAAGCAACGCCAGACACTCAGGAAAATGGTGATTGACATGGTGTTAGCAACTGATATGTCCAAGCACATGATGAGCCTCCTGGCTGACCTTAAAACGATGGTAGAA
LysLysGlnArgGlnThrLeuArgLysMETValIleAspMETValLeuAlaThrAspMETSerLysHisMETSerLeuLeuAlaAspLeuLysThrMETValGlu

```
GAGGACAACCGGGACTGGTACTACAGCGCCATCTCCGGCAGAGCCCATCTCCCCACCCGAGGAGGAGTCAAGGGGCCAGGCCACCACCCCTGCCTGACAAG
GluAspAsnArgAspTrpTyrTyrSerAlaIleArgGlnSerProSerProProGluGluGluSerArgGlyProGlyHisProProLeuProAspLys

TTCCAGTTTGAGCTGACGCTGGAGGAGGAGGAAGAGAGAGAAATATCAATGCCCAGATACCGTGCACAGAGGCATTGACTGAGCAGGATTGTCA
PheGlnPheGluLeuThrLeuGluGluGluGluGluGluIleSerMETAlaGlnIleProCysThrAlaGlnIleProCysThrAlaGlnIleAlaLeuThrGluGlnGlyLeuSer

GGAGTCGAGGAAGCTCTGATGCAACCATAGCCTGGGAGGCATCCCGGCCCAGGAGTCGTTGGAAGTTATGCACAGGAAGCATCCTGGAGGCCGAGCTG
GlyValGluAlaLeuAspAlaThrIleAlaTrpGluAlaSerProAlaGlnGluSerLeuGluValMETAlaGlnGluAlaSerLeuGluAlaGluLeu

GAGGCAGTGTATTTGACACAGCAGGACGCCACAGTCCACGGCCAGTGCACCTGTGCCTCCGATGAGTTCTGTCCCGGAGGAATTCGTGTTGCTGTAAGCCAC
GluAlaValTyrLeuThrGlnGlnAlaGlnSerThrGlySerAlaProValAlaProAspGluPheSerSerArgGluPheValAlaValSerHis

AGCAGCCCCTCTGCCCTCTTCAAAGCCCCCTGTCTCTGTTTCAGAGACATGCCCGGCCTCCCCGGCCTCCCTCCACGGC
SerSerProSerAlaLeuAlaLeuGlnSerProLeuLeuProAlaLeuProAlaTrpArgThrLeuSerValSerGluHisAlaArgProProGlyProProLeuHisGly

GGCCGAGGTGGAGGCCCAACGAGCACCAGGCTGCCAAGAGGGCTTGCAGTGCCTGCCAGGACATTTGGGAGGACACATCCCAGCTCCTGG
GlyArgGlyGlyGlyProThrArgAlaProGlyCysGlnGluGlyLeuGlnCysLeuArgArgAspIleTrpGlyGlyHisIleArgThrProSerSerTrp

TGGCGGGGGTCAGGTGGAGACCCTACCTGATCCCCAGACCTCTGTCCCTAGACCCTCCCTGTCCCCCTCACTCCCCTGTCCCCCGACCACCTCCTCCT
TrpArgGlyValArgTrpArgProTyrLeuIleProArgProLeuSerLeuPheProSerThrProProLeuThrProLeuLeuProArgProProProPro

CTGCCTCAAAGACTCTTGTCCTCTTGTCCGGCCGCAAGCTT
LeuProGlnArgLeuLeuSerSerCysProArgProGlnAla
```

60  AAGCTTGCGGGCCGCATTGGGTACCGCGTGCCAGCAGGCAGTGCCCTAGCCTTCCGCCT
     ATGCCCTCCCTCCAAGAGGTGACTGCGCTCCCCCAGCAGCTGCCTGAGGAGGGGTGCCAGGTCCCGGGGG
  1  METProSerLeuGlnGluValThrAlaLeuProSerSerSerGluGluGlyValProGlySerArgGly
     AGCCCCAGCGACCTCACCCCCACCTGGGCGCCGACCTCTGCTTCCGGTCCATGAGCGCCTTCTGCTCCTA
     SerProAlaThrSerProHisLeuGlyArgArgArgProLeuLeuGlyArgSerMETSerAlaAlaPheCysSerLeu
     CTGGCACCGGAGCGGCAGGTGGGCCGGCTGCGGCAGCAGCACTGATGCAGGACCGACACACAGCCGGGCCAGCTG
     LeuAlaProGluArgGlnValGlyArgAlaAlaAlaAlaLeuMETGlnAspArgHisThrAlaAlaGlyGlnLeu
     GTGCAGGACCTACTGACCCAGGTGCGGGATGGGCAGAGGGCAGAGCTCGAGGGCATCCGTCAGGCGCTGAGC
     ValGlnAspLeuLeuThrGlnValArgAspGlyGlnArgProGlnLeuGluGlyIleArgGlnAlaLeuSer
     CGGGGCCCGGGCCATGCTGAGTGCGGAGCTGGCCCTAAGAGCTGAACATGTCCTG
     ArgAlaArgAlaMETLeuSerAlaGluLeuGlyProGluLysArgLeuValSerProLysArgLeuHisValLeu
     GAGAAGTCATTGCATTGCTCTGTGCTCAAGCCTCTCCGGCCCATCCTGGCAGCCCGCAGCCCGGGCCTTGCC
     GluLysSerLeuHisCysSerValLeuLysProLeuArgProIleLeuAlaAlaArgArgArgLeuAla
     GCAGACGGCTCCCTGGGCCGCCTAGCTGAGGGCCTCGGGGCCCCAGGGCCCGGAGCCTTCGGGTCC
     AlaAspGlySerLeuGlyArgLeuAlaGluAlaArgAlaArgAlaGlnGlyProGlyAlaPheGlySer
```

FIG. 5A

CACCCTGAGCCTGCCCTCCCCAGTAGAGTTGGAGCAAGTGCGCCAGAAGCTGCTGCAGCTCGTCCGCACCTACTCA
HisLeuSerProValGluLeuGluGlnValArgGlnLysLeuLeuGlnLeuValArgThrTyrSer

CCCAGCGGCCAGGTCAAGGGCTCCTGCAAGCTGCTCTACATGGCCCTGAGGACCCAGGAAGGGGAG
HisLeuSerProValGluLeuGluGlnValArgGlnLysLeuLeuGlnLeuValArgThrTyrSer

ProSerAlaGlnValLysArgLeuLeuGlnAlaCysLysLeuLeuTyrMETAlaLeuArgThrGlnGluGlyGlu

GGCTCGGGTGCCGACGGGTTCCTGCTGAGCCTCGTCTTGGCCACTGTGACCTTCCTGAGCTGCTG
GlySerGlyAlaAspGlyPheLeuProLeuLeuSerLeuValLeuAlaHisCysAspLeuProGluLeuLeuLeu

GAGGCCGAGTACATGTCGGAGCTGCTGGAGCCTGCTACTGGGAGAGGGTGGCTACTACCTGACCAGCCTC
GluAlaGluTyrMETSerGluLeuLeuGluProSerLeuLeuThrGlyGluGlyGlyTyrTyrLeuThrSerLeu

TCTGCCAGCCTGGCCCTGCTGAGTGGCCTGGGTCAGGCCCCACACCCTCCCACTGAGCCCCGTGCAGGAGCTACGG
SerAlaSerLeuAlaLeuLeuSerGlyLeuGlyGlnAlaHisThrLeuProLeuSerProValGlnGluLeuArg

CGCTCCCTCAGCCCTCTGGGAGCAGGCGCTGCCTGCCAGCACCTCCTCCAGCACCTGCTTCCAGCACTGCCTAT
ArgSerLeuSerLeuTrpGluGlnArgArgLeuProAlaThrHisCysPheGlnHisLeuLeuArgValAlaTyr

FIG. 5B

```
CAGGATCCCAGCAGTGGCTGCACCTCCAAGACCCTGGCCGTGCCCCAGAGGCCTGATTGCCACCCTGAACCAG
GlnAspProSerSerGlyCysThrSerLysThrLeuAlaValProProGluAlaSerIleAlaThrLeuAsnGln
CTCTGTGCCACCAAGTTCCGAGTGACCCAGCCCAACACTTTTGGCCTCTTCCTGTACAAGGAGCAGGCTACCAC            405
LeuCysAlaThrLysPheArgValThrGlnProAsnThrPheGlyLeuPheLeuTyrLysGluGlnGlyTyrHis
CGCCTGCCCCCTGGGCCCTGCCCCACAGGCTGCCACCACTGTCTACCTGTCCGGGCAGAGTGGCCTG
ArgLeuProProGlyProTrpProThrGlyCysProProLeuAlaThrSerSerThrAlaGlyGlnSerGlyLeu
AGACCCAGGGGCTGTGACAGAGGAGGGCAGTGGGCAGTCAGAGGCAAGAAGCAGAGGGGAGGAGCAAGGGT
ArgProArgGlyLeu
GCCAGGGAGATGGGGATGCTGGGGTCAAAGCCAGGGACATTCGGGAACAGTCTGAGACAACTGCTGAAG
GGGGCCAGGGTCAAGGCCCAGGAAGCCCTGCTCAGCCAGGGAACCAGAGGCCAGAGGGAAGCCCGGGCAGCAGAGG
AGTAGCTTGAAGTGGCCAGAAGGGTCATTCGGGGAGACCCTGAGCCTGCTGAGAAATCCTTTTAGCGCCAG
CAAGCCCCACCCAGGGCCCTGTCCTGTCTGCCACCACCTTTGTCTGATACTTGTTTCCAGGGAAGCTGGGGGA
ACTGCCACATCTGAGGAACTGGAATAAAGATGAGGGGCCTTCGGGGCCAATGCGGGCCGCGGGCCTTTTTGGC             1721
CAGCTCGAATTC
```

```
                                                                                    GCGGCCGCCGGCCGGCAGGGCTGAGCCGAC
30  ATGAGCATTTCTACTTCCTCCTCCGACTCGCTGGAGTTCGACCGGAGCATGCCTCTGTTTGGCTACGAGGCGGAC
 1  METSerIleSerThrSerSerSerAspSerLeuGluPheAspArgSerMETProLeuPheGlyTyrGluAlaAsp

ACCAACAGCAGCCTGGAGGACTACGAGGGGAAAGTGACCAAGAGACCATGGCGCCCCCATCAAGTCCAAAAAG
    ThrAsnSerSerLeuGluAspTyrGluGlyLysValThrLysArgProTrpArgProIleLysSerLysLys

AAAAGGAGCAGCTCCTTCGTGCTGCCCAAGCTCGTCAAGTCCCAGCTGCAGAAGGTGAGCGGGGTGTTCAGCTCC
    LysArgSerSerSerPheValLeuProLysLeuValLysSerGlnLeuGlnLysValSerGlyValPheSerSer

TTCATGACCCCGGAGAAGCGGATGGTCCGCAGGATCGCCGAGCTTTCCCGGACAAATGCACCTACTTCGGGTGC
    PheMETThrProGluLysArgMETValArgArgIleAlaGluLeuSerArgAspLysCysThrTyrPheGlyCys

TTAGTGCAGGACTACGTGAGCTTCCTGCAGGAGAACAAGGAGTGCCACGTGTCCAGCACCGACATGCTGCAGACC
    LeuValGlnAspTyrValSerPheLeuGlnGluAsnLysGluCysHisValSerSerThrAspMETLeuGlnThr

ATCCGGCAGTTCATGACCCAGTTCAAGAACTATTTGTCTCAGAGCTCGGACCCCCATCGAGTCGCTG
    IleArgGlnPheMETThrGlnValLysAsnTyrLeuSerGlnSerSerGluLeuAspProIleGluSerLeu

ATCCCTGAAGACCAAATAGATGTGGTGCTGGAAAAAGCCATGCACAAGTGCATCTTGAAGCCCCTCAAGGGCCAC
    IleProGluAspGlnIleAspValValLeuGluLysAlaMETHisLysCysIleLeuLysProLeuLysGlyHis
```

FIG. 6A

GTGGAGGCCATGCTGAAGGACTTTCACATGGCCGATGGCTCATGGAAGCAACTCAAGGAGAACCTGCAGCTTGTG
ValGluAlaMETLeuLysAspPheHisMETAlaAspGlySerTrpLysGlnLeuLysGluAsnLeuGlnLeuVal

CGGCAGAGGAATCCGCAGGAGCTGGGGGTCTTCGCCCCGACCCCTGATTTTGTGGATGTGGAGAAAATCAAAGTC
ArgGlnArgAsnProGlnGluLeuGlyValPheAlaProThrProAspPheValAspValGluLysIleLysVal

AAGTTCATGACCATGCAGAAGATGTATTCGCCGGAAAAGAAGGTCATGCTGCTCTGCGGGTCTGCTCAAGCTCATT
LysPheMETThrMETGlnLysMETTyrSerProGluLysLysValMETLeuLeuArgValCysLysLeuIle

TACACGGTCATGGAGAACAACTCAGGGAGGATGTATGGCGCTGATGACTTCTTGCCAGTCCTGACCTATGTCATA
TyrThrValMETGluAsnAsnSerGlyArgMETTyrGlyAlaAspAspPheLeuProValLeuThrTyrValIle

GCCCAGTGTGACATGCTTGAATTGGACACTGAAATCGAGTACATGATGGAGCTCCTAGACCCATCGCTGTTACAT
AlaGlnCysAspMETLeuGluLeuAspThrGluIleGluTyrMETMETGluLeuLeuAspProSerLeuLeuHis

GGAGAAGGAGGCTATTACTTGACAAGCGCATATGGAGCACTTTCTCTGATAAAGAATTTCCAAGAAGAACAAGCA
GlyGluGlyGlyTyrTyrLeuThrSerAlaTyrGlyAlaLeuSerLeuIleLysAsnPheGlnGluGluGlnAla

GCGCGACTGCTCAGCTCAGAAACCAGAGACACCCTGAGGCAGTGGCACAAACGGAGAACCACCAACCGGACCATC
AlaArgLeuLeuSerSerGluThrArgAspThrLeuArgGlnTrpHisLysArgArgThrThrAsnArgThrIle

FIG. 6B

CCCTCTGTGGACGACTTCCAGAATTACCTCCGAGTTGCATTCAGGAGTCAACAGTGTTGCACAGGAAAGACC
ProSerValAspAspPheGlnAsnTyrLeuArgValAlaPheGlnGluValAsnSerGlyCysThrGlyLysThr

CTCCTTGTGAGACCTTACATCACCACTGAGGATGTGTGTCAGATCTGCGCTGAGAAGTTCAAGGTGGGGACCCT
LeuLeuValArgProTyrIleThrThrGluAspValCysGlnIleCysAlaGluLysPheLysValGlyAspPro

GAGGAGTACAGCCTCTTTCTCTTCGTTGACGAGACATGGCAGCAGCTGGCAGAGGACACTTACCCTCAAAAAATC
GluGluTyrSerLeuPheLeuPheValAspGluThrTrpGlnGlnLeuAlaGluAspThrTyrProGlnLysIle

AAGGCGGAGCTGCACCAGCCGACCACAGCCCCACATCTTCCACTTTGTCTACAAACGCATCAAGAACGATCCTTAT
LysAlaGluLeuHisSerArgProGlnProHisIlePheHisPheValTyrLysArgIleLysAsnAspProTyr

GGCATCATTTTCCAGAACGGGGAAGAAGACCTCACCACCTCCTAGAAGACAGGCGGGACTTCCCAGTGGTGCATC
GlyIleIlePheGlnAsnGlyGluGluAspLeuThrThrSer

CAAAGGGGAGCTGGAAGCCTTGCCTTCCCGCTTCTACATGCTTGAGCTTGAAAAGCAGTCACCTCCTCGGGACC

CCTCAGTGTAGTGACTAAGCCATCCACAGGCCAACTTTAGCCACGCAAGGTAGCTGAGGT

TTGTGAAACAGTAGGATTCTCTTTTGGCAATGGAGAATTGCATCTGATGGTTCAAGTGTCCTGAGATTGTTTGCT

ACCTACCCCCAGTCAGGTTGGCTTACAGGTATGTATATGTGCAGAAGAAAACACTTAAGATACAAGTTC

TTTTGAATTCAACAGCAGATGCTTGCGATGCAGTCGTCAGGTGATTCTCACTCCTGTGGATGGCTTCATCCCTG

1   GGCCGCATTGCCGACCCGGCCCGTAGTGTGGAAGCAGCTTCAGCTTCAAAGATTAGAACGACTCCGAAAGAGAGA
1   GlyArgIleAlaAspProAlaArgSerValGluAlaAlaSerAlaGlnArgLeuGluArgLeuArgLysGluArg

CAAAACCAGATCAAATGCAAAAATATTCAGTGGAAAGAAAGAAATTCTAAGCAATCAGCCCAGGAGTTAAAGTCA
    GlnAsnGlnIleLysCysLysLysAsnIleGlnTrpLysGluArgAsnSerAlaGlnGluLeuLysSer

CTGTTTGAAAAAAAATCTCTCAAAGAGAAGCCTCCAATTTCTGGAAGCAGTCGATATTATCTGTACGCCTAGAA
    LeuPheGluLysLysSerLeuLysGluLysProProIleSerGlyLysGlnSerIleLeuSerValArgLeuGlu

CAGTGCCCTCTGCAGCTGAATAACCCTTTTAACGAGTATTCCAAATTTGATGGCAAGGTCATGTAGGTACAACA
    GlnCysProLeuGlnLeuAsnAsnProPheAsnGluTyrSerLysPheAspGlyLysPheHisValGlyThrThr

GCAACCAAGAAGATCGATGTCTACCTCCCCTCTGCACTCGAGCCAGGACAGAGATGCTGCCAATGACCGTGGTGACA
    AlaThrLysLysIleAspValTyrLeuProLeuHisSerSerGlnAspArgLeuLeuProMETThrValThr

ATGGCCAGGCCAGGGTGCAGGACCTGATCGGGCTCATCTGCTGGCAGTATACAAGCGAAGGACGGGAGCCGAAG
    METAlaSerAlaArgValGlnAspLeuIleGlyLeuIleCysTrpGlnTyrThrSerGluGlyArgGluProLys

FIG. 7A

```
CTCAATGACAATGTCAGTGCCTACTGCCTGCATATTGCTGAGGATGATGGGGAGTGGACACCGATTCCCCCG
LeuAsnAspAsnValSerAlaTyrCysLeuHisIleAlaGluAspAspGlyGluValAlaAspThrAspPheProPro

CTGGATTCCAATGAGCCCATTCATAAGTTTGGCCTTCAGTACTTTGGGCCCTGTTGAAAAGTACTCATCTCCTGGT
LeuAspSerAsnGluProIleHisLysPheGlyPheSerThrLeuAlaLeuValGluLysTyrSerSerProGly

CTGACATCCAAAGAGTCACTCTTTGTTCGAATAAATGCTGCTCATGGATTCTCCCTTATTCAGGTGGACAACACA
LeuThrSerLysGluSerLeuPheValArgIleAsnAlaAlaHisGlyPheSerLeuIleGlnValAspAsnThr

AAGGTTACCATGAAGGAAATCTTACTGAAGGCAGTGAAGCGAAGAAAAGGATCCCAGAAAGTTTCAGGCCCTCAG
LysValThrMETLysGluIleLeuLeuLysAlaValLysArgArgLysGlySerGlnLysValSerGlyProGln

TACCGCCTGGAGAAGCAGAGCCCAATGTCGCCGTTGACCTGGACAGCACTTTGGAGAGCCAGAGCGCATGG
TyrArgLeuGluLysGlnSerGluProAsnValAlaValAspLeuAspSerThrLeuGluSerGlnSerAlaTrp

GAGTTCTGCCTGGTCCGCGAGAACAGTTCAAGGGCAGACGGGGTTTTTGAGGAGGATTCGCAAATTGACATAGCC
GluPheCysLeuValArgGluAsnSerSerArgAlaAspGlyValPheGluGluAspSerGlnIleAspIleAla
```

FIG. 7B

```
ACAGTACAGGATATGCTTAGCAGCCACCATTACAAGTCATTCAAAGTCAGCATGATCCACAGACTGCGATTCACA
ThrValGlnAspMETLeuSerSerHisHisTyrLysSerPheLysValSerMETIleHisArgLeuArgPheThr

ACCGACGTACAGCTAGGTATCTCTGGAGACAAAGTAGAGATAGACCCTGTTACGAATCAGAAAGCCAGCACTAAG
ThrAspValGlnLeuGlyIleSerGlyAspLysValGluIleAspProValThrAsnGlnLysAlaSerThrLys

TTTTGGATTAAGCAGAAACCCATCTCAATGATTCCGACCTGCTCTGTGCCTGTGAAGAGAAAAGC
PheTrpIleLysGlnLysProIleSerIleAspSerAspLeuLeuCysAlaCysAspLeuAlaGluLysLysSer

CCCAGTCACGCAATATTAAACTCAGTATCTAAGCAATCACGACTATAAACACCTCTACTTTGAATCGGACGCT
ProSerHisAlaIlePheLysLeuPheLysLeuThrTyrLeuSerAsnHisAspTyrLysPheGluSerAspAla

GCTACCGTCAATGAAATTGTGCTCAAGGTTAACTACATCCTGGAATCGCGAGCACTGCCCGGGCTGACTAC
AlaThrValAsnGluIleValLeuLysValAsnTyrIleLeuGluSerArgAlaSerThrAlaArgAlaAspTyr

TTTGCTCAAAAAAAAGCGGCCGC          1301
PheAlaGlnLysLysSerGlyArg          434
```

FIG. 7C

CLONING OF MAMMALIAN GENES IN MICROBIAL ORGANISMS AND METHODS FOR PHARMACOLOGICAL SCREENING

FUNDING

Work described herein was supported by the National Cancer Institute of the National Institutes of Health.

DESCRIPTION

BACKGROUND OF THE INVENTION

Presently, there are several methods available for cloning mammalian genes. The standard approach to cloning mammalian genes requires obtaining purified protein, determining a partial amino acid sequence of the purified protein, using the partial amino acid sequence to produce degenerate oligonucleotide probes, and screening cDNA libraries with these probes in order to obtain cDNA encoding the protein. This method is time consuming and, because of the degeneracy of the probes used, may identify sequences other than those encoding the protein(s) of interest. Many mammalian genes have been cloned this way, including the cGMP phosphodiesterase expressed in retina (Ovchinnikov, Y-A. et al., FEB 223: 169 (1987)).

A second approach to cloning genes encoding a protein of interest is to use a known gene as a probe to find homologs. This approach is particularly useful when members of a gene family or families are sufficiently homologous. It is reasonable to expect that members of a given gene family can be so cloned once one member of the family has been cloned. The D. melanogaster dunce phosphodiesterase gene was used, for example to clone rat homologs. (Davis, R. L. et al., Proc. Natl. Acad. Sci. USA 86: 3604 (1989); Swinnen, J. V. et al., Proc. Natl. Acad. Sci. USA 86: 5325 (1989)). Although members of one family of phosphodiesterase genes might be cloned once a member of that family has been cloned, it is unclear whether the nucleotide sequences of genes belonging to different phosphodiesterase gene families exhibit sufficient homology to use probes derived from one family to identify members of another family.

It would be useful to have a method which could be used to clone genes which does not have the limitations of presently available techniques.

SUMMARY OF THE INVENTION

The present invention relates to a method of cloning mammalian genes encoding proteins which can function in microorganisms, particularly yeast, and can modify, complement, or suppress a genetic defect associated with an identifiable phenotypic alteration or characteristic in the microorganism. It further relates to mammalian genes cloned by the present method, as well as to products encoded by such genes and antibodies which can bind the encoded proteins. More specifically, the present invention relates to a method of cloning mammalian genes which encode products which modify, complement or suppress a genetic defect in a biochemical pathway in which cAMP participates or in a biochemical pathway which is controlled, directly or indirectly, by a RAS protein, to products (RNA, proteins) encoded by the mammalian genes cloned in this manner and to antibodies which can bind the encoded proteins. As described herein, the present method has been used to identify novel mammalian genes which encode cAMP phosphodiesterases and proteins which interact with RAS proteins. These genes, and others that can be derived by the claimed method, are part of this invention, as are the proteins which they encode.

The present invention further relates to a method of identifying agents which alter (i.e., reduce or stimulate) the activity of the protein products of such mammalian genes expressed in microorganisms, such as yeast. Identification of such agents can be carried out using two types of screening procedures: one based on biochemical assays of mammalian proteins of known enzymatic function and one based on phenotypic assays for proteins of unknown function. In the former case, if the encoded proteins are cAMP phosphodiesterases, pharmacological screens include the assay for agents which alter (i.e., reduce or stimulate) phosphodiesterase activity. In the latter case, if the encoded proteins interact with RAS proteins, pharmacological screens include the assay for agents which reduce or stimulate interactions with RAS proteins.

BRIEF DESCRIPTION OF THE DRAWINGS

FIG. 2 (parts A–B) is a schematic representation of the yeast expression vectors used to clone mammalian cDNAs.

In FIG. 2B, the stippled area indicates a portion of the ADH coding sequences.

FIG. 3 is the nucleotide sequence of DPD cDNA (top line) and its deduced amino acid sequence (bottom line). Nucleotide and amino acid coordinates are given in the left hand margin.

FIG. 4 is the nucleotide sequence and the deduced amino acid sequence of cDNA clone #44. Nucleotide and amino acid coordinates are given in the left hand margin.

FIG. 5 is the nucleotide sequence and the deduced amino acid sequence of cDNA clone #99. Nucleotide and amino acid coordinates are given in the left hand margin.

FIG. 6 is the nucleotide and the deduced amino acid sequence of cDNA clone #265. Nucleotide and amino acid coordinates are given in the left hand margin.

FIG. 7 is the nucleotide sequence and the deduced amino acid sequence of cDNA clone #310. Nucleotide and amino acid coordinates are given in the left hand margin.

DETAILED DESCRIPTION OF THE INVENTION

Figure 1:
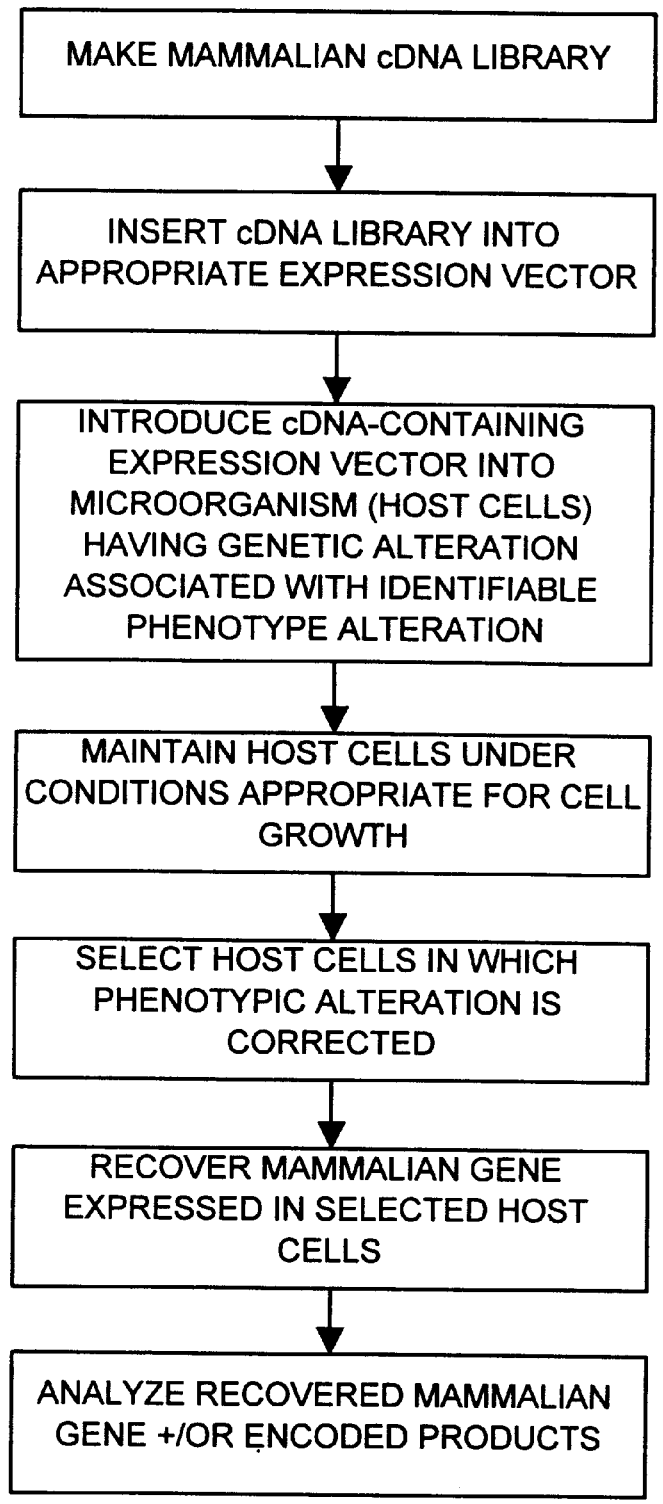
FIG. 1 is a flow diagram of the steps of the present method of cloning a mammalian gene which encodes a product capable of correcting a genetic alteration in a microorganism which is associated with an identifiable phenotypic characteristic.

The present invention relates to a method of cloning a mammalian gene which, when expressed in a microorganism, can modify, complement or suppress, in the microorganism, a genetic alteration or defect which is associated with an identifiable phenotype. Cloning of a selected mammalian gene is carried out according to the present method by introducing the gene into a genetically altered microorganism which has an identifiable phenotypic alteration or characteristic associated with the genetic alteration;

maintaining the genetically altered microorganism in which the gene is present under conditions appropriate for cell growth; and selecting cells in which the phenotypic alteration or characteristic is modified as a result of correction, complementation or suppression of the genetic alteration or defect by the introduced mammalian gene. The present invention further relates to mammalian genes cloned by the present method, products (e.g., RNA, proteins) encoded by such genes and antibodies specific for encoded proteins. In particular, the present invention relates to a method of cloning and isolating a selected mammalian gene which, when expressed in yeast having a genetic alteration or defect associated with an identifiable phenotypic characteristic or alteration, corrects, complements or supplements the genetic alteration and modifies or corrects the associated phenotypic characteristic.

Through use of the method described herein, mammalian genes capable of modifying phenotypic alterations in yeast associated with activation or attenuation of biochemical pathways in which cAMP participates or with biochemical pathways which interact with or are controlled by RAS proteins have been identified, cloned and characterized. As described herein, the subject method has been used to clone mammalian genes encoding cAMP phosphodiesterases or proteins which interact with a RAS protein. This has been accomplished using yeast cells in which there is a genetic alteration in the RAS2 gene and which, as a result, are heat shock sensitive. Additional mammalian genes having these same characteristics can be identified, cloned and characterized using the method described. In each case, an appropriately-selected genetically altered host cell (e.g., yeast) is used for expression of the selected mammalian gene, which generally is introduced as one component of a gene library. The genetic alteration in the host cell is selected in such a manner that it is associated with an identifiable phenotypic characteristic which is corrected upon expression of the mammalian gene. The genetic alteration can be a deletion of a gene or a portion of a gene, a change in nucleotide sequence or any other nucleotide manipulation which renders a gene unable to function normally. The genetic alteration is selected in such a manner that a gene of interest can be identified when it is expressed in the altered host cell.

The mammalian genes, when expressed in yeast containing a genetic defect in a biochemical pathway, can correct, complement or alter the genetic defect and correct the phenotypic alteration (i.e., produce a phenotype more like that of normal or unaltered yeast). Cells containing the mammalian gene to be cloned are identified on the basis of correction or suppression of the phenotypic characteristic. The correction or suppression need not be complete.

As described herein, it is now possible to identify inhibitors and activators of cAMP phosphodiesterases, which can be used therapeutically to control or regulate cAMP levels or activity. In addition, it is now possible to identify agents which inhibit or stimulate interaction of gene products with RAS proteins.

It is one of the objects of this invention to discover, isolate and characterize new genes encoding cAMP phosphodiesterases. It is a further object of this invention to describe methods for identifying chemical agents which inhibit or stimulate cAMP phosphodiesterases and can be used for therapeutic purposes. Both of these objectives can be achieved through use of methods, described herein, for cloning genes encoding cAMP phosphodiesterases and expressing the proteins that they encode in cells with little or no other cAMP phosphodiesterase activity. Typically, cells used for expressing the proteins to be analyzed for cAMP phosphodiesterase activity lack other cAMP phosphodiesterase activity. Extracts from such cells thus provide a means by which agents which alter cAMP phosphodiesterases can be identified and isolated.

It is one of the further objects of this invention to discover, isolate and characterize new genes encoding products that interact with RAS proteins. It is still a further object of this invention to describe methods for identifying agents which inhibit or stimulate the interaction of these new gene products with RAS. This is accomplished through use of methods described herein for cloning genes encoding proteins that interact with RAS, and expressing the encoded proteins in cells that have phenotypes which are sensitive to the activity of these proteins.

The following is a description of cAMP phosphodiesterases; pathways controlled by RAS proteins; use of the present method for identification of mammalian genes, exemplified by identification of genes encoding cAMP phosphodiesterases and genes encoding products which interact with RAS proteins; use of the method to screen for agents which inhibit or stimulate cAMP phosphodiesterases; screening for agents which inhibit or stimulate interaction of such proteins with RAS proteins; and uses of the invention.

cAMP Phosphodiesterases

Adenylyl cyclase is an ubiquitous enzyme which generates cyclic adenosine monophosphate (cAMP). cAMP is a universal "second messenger" in both eukaryotes and prokaryotes. In eukaryotes, cAMP exerts its profound effects on cellular physiology by stimulating a cAMP-dependent protein kinase (Robinson, G. A., et al., *In Cyclic AMP*, Academic Press (1971)). This kinase is composed of regulatory and catalytic subunits. The regulatory subunits combine with and inhibit the catalytic subunits. When the regulatory subunits bind cAMP, they release the catalytic subunits, which in turn phosphorylate proteins on serine and threonine residues. The genes encoding the catalytic and regulatory subunits have been cloned from yeast and mammals (Toda, T., et al., *Cell* 50: 277 (1987); Shoji, S., et el., *Biochemistry* 22: 3702 (1983); Showers, M. O. and Mauver, R. A., *J. Biol. Chem.* 261: 16288 (1986); Titani, K., et al., *Biochemistry* 23: 4193 (1984); Takio, K., et al, *Biochemistry* 23: 4200 (1984)).

In mammals, cAMP is generated by cells in response to hormones, growth factors, and neurotransmitters (Robison, G. A. et al., *Cyclic AMP*, Academic Press, New York and London (1971)). The concentration of cAMP in mammalian cells is determined not only by its rate of production by adenylyl cyclase, but also by its rate of degradation by enzymes called phosphodiesterases, or more specifically, cAMP phosphodiesterases.

A number of important physiological responses in humans are controlled by cAMP levels, including mental function, smooth muscle relaxation, strength of cardiac contractility, release of histamine and other immunoreactive molecules, lymphocyte proliferation and platelet aggregation (Robison, G. A. et al., *Cyclic AMP*, Academic Press, New York and London (1971)). Thus, the range of diseases which can potentially be affected by agents or pharmaceutical compounds which alter cAMP levels include inflammatory processes (e.g., arthritis and asthma), heart failure, smooth muscle cramps, high blood pressure, blood clotting, thrombosis, and mental disorders. One way to modulate cAMP levels in cells is through the modulation of cAMP phosphodiesterase activity.

Many drugs which raise cAMP levels in various tissues are in common use. These drugs are useful in treating heart failure, asthma, depression, and thrombosis. Only a few of these drugs appear to work by inhibiting cAMP phosphodiesterases. The pharmaceutical industry has not been notably successful at finding such drugs, since effective drug screens have not been available. The reasons for this are set forth below.

Most tissues contain so many different isoforms of phosphodiesterases that drug screening based on inhibition of crude tissue extracts is unlikely to yield anything other than a broadly acting inhibitor of phosphodiesterases. Broadly acting inhibitors of cAMP phosphodiesterases, such as theophylline, have many deleterious side effects. A few inhibitors are known which have narrow specificity. Such inhibitors may have great potential utility because they can target phosphodiesterases in one or a few tissue and cell types and thus have a higher therapeutic index.

The yeast cAMP phosphodiesterase genes PDE1 and PDE2 were the first phosphodiesterase genes cloned (Sass, P., et al., *Proc. Natl. Acad. Sci. USA,* 83:9303 (1986); Nikawa, J., et al., *Mol. Cell. Biol.,* 7:3629 (1987)). Comparison of the amino acid sequence of the yeast phosphodiesterases to the amino acid sequences of other eukaryotic phosphodiesterases reveals only limited sequence homology. PDE2 has very slight sequence homology to the dunce phosphodiesterase of *D. melanogaster* and to two phosphodiesterases expressed in bovine heart and brain (Charbonneau, H., et. al., *Proc. Natl. Acad. Sci.,* 83: 9308 (1986)). PDE1 shares even less of this homology, but resembles to a greater extent a secreted form of phosphodiesterase found in *D. discoidem* (Nikawa, J., et al., *Mol. Cell. Biol.* 7: 3629 (1987)). Thus, there appear to be many diverse branches of cAMP phosphodiesterase genes in evolution.

Biochemical, serological and pharmacological studies strongly suggest the existence of multiple families of cAMP phosphodiesterases in mammals (Beavo, J. A. *Advances in Second Messenger* and *Phosphoprotein Research* Vol. 22 1 (1988)). Partial amino acid sequence data and recent nucleic acid sequence data confirm this (Charbonneau, H., et al., *Proc. Natl. Acad. Sci., USA* 83: 9308 (1986); Colicelli, J., et al., *Proc. Natl. Acad. Sci. USA* 86: 3566 (1989); Davis, R. L., et al., *Proc. Natl. Acad. Sci. USA* 86: 3604 (1989); Swinnen, J. V., et al., *Proc. Natl. Acad. Sci. USA* 86: 5325 (1989)).

The various known phosphodiesterases fall into several classes: (I) $Ca^{++}$/calmodulin dependent, (II) cGMP stimulated, (III) cGMP inhibited, (IV) high affinity cAMP, (V) cGMP and (VI) nonspecific phosphodiesterases. Each class may be made up of a family of related proteins. In some cases these related proteins may be encoded by separate genes and in other cases they may arise from alternative gene splicing. Generally, a tissue expresses multiple classes of phosphodiesterases, which, by their copurification and proteolytic degradation, render biochemical analysis exceedingly difficult. The analysis of this complexity is aided somewhat by the availability of a few pharmacological agents which discriminate between different classes of phosphodiesterases, and, recently, by serological reagents which can distinguish between families and sometimes between members of a family (Beavo, J. A. *Advances in Second Messenger and Phosphoprotein Research* Vol. 22: 1–38 (1988)).

The classification of mammalian phosphodiesterases may not be complete, however. New families and types of activities may yet be discovered. The great majority of the cAMP phosphodiesterase genes have not yet been cloned.

Pathways Controlled by RAS Proteins

The RAS genes were first discovered as the transforming principles of the Harvey and Kirsten murine sarcoma viruses (Ellis, R. W., et al., *Nature* 292: 506 (1981)). The cellular homologs of the oncogenes of Harvey and Kirsten murine sarcoma viruses (H-RAS and K-RAS) constitute two members of the RAS gene family (Shimizu, K et al., *Proc. Natl. Acad. Sci.* 80:2112 (1983)). A third member is N-RAS (Shimizu, K. et al., *Proc. Natl. Acad. Sci.* 80: 2112 (1983)). These genes are known as oncogenes since point mutations in RAS can result in genes capable of transforming noncancerous cells into cancerous cells (Tabin, C. J., et al., *Nature* 300: 143 (1982); Reddy, E. P., et al., *Nature* 300: 149 (1982); Taparowsky, E., et al., *Nature* 300: 762 (1982);). Many tumor cells contain RAS genes with such mutations (Capon, D. J., et al., *Nature* 302:33 (1983); Capon, D. J., et al., *Nature* 304: 507 (1983); Shimizu, K. et al., *Nature* 304: 497 (1983); Taparowsky, E., et al., *Cell* 34: 581 (1983); Taparowsky, E., et al., *Nature* 300: 762 (1982); Barbacid, M., *Ann. Rev. Biochem.* 56: 779 (1987)).

Despite the importance of the RAS oncogenes to our understanding of cancer, the function of RAS genes in mammals is not known. The RAS proteins are small proteins (21,000 daltons in mammals) which bind GTP and GDP (Papageorge, A., et al., *J. Virol.* 44: 509 (1982)). The RAS proteins hydrolyze GTP slowly; specific cellular proteins can accelerate this process (McGrath, J. P., et al., *Nature* 310: 644 (1984); Trahey, M., et al., *Science* 238: 542 (1987)). RAS proteins bind to the inner surface of the plasma membrane (Willingham, M. C., et al., *Cell* 19: 1005 (1980)) and undergo a complex covalent modification at their carboxy termini (Hancock, J. F., et al., *Cell* 57: 1167 (1989)). The crystal structure of H-RAS is known (De Vos, A. M. et al., *Science* 239: 888 (1988)).

The yeast Saccharomyces cerevisiae contains two genes, RAS1 and RAS2, that have structural and functional homology with mammalian RAS oncogenes (Powers, S., et al., *Cell* 36: 607 (1984); Kataoka, T., et al., *Cell* 40: 19 (1985) Defeo-Jones, D. et al., *Science* 228: 179 (1985); Dhar, R., et al., *Nucl. Acids Res.* 12: 3611 (1984)). Both RAS1 and RAS2 have been cloned from yeast plasmid libraries and the complete nucleotide sequence of their coding regions has been determined (Powers, S., et al., *Cell* 36: 607 (1984); DeFeo-Jones, D., et al., *Nature* 306: 707 (1983)). The two genes encode proteins with nearly 90% identity to the first 80 amino acid positions of the mammalian RAS proteins, and nearly 50% identity to the next 80 amino acid positions. Yeast RAS1 and RAS2 proteins are more homologous to each other, with about 90% identity for the first 180 positions. After this, at nearly the same position that the mammalian RAS proteins begin to diverge from each other, the two yeast RAS proteins diverge radically. The yeast RAS proteins, like proteins encoded by the mammalian genes, terminate with the sequence cysAAX, where A is an aliphatic amino acid, and X is the terminal amino acid (Barbacid, M., *Ann., Rev. Biochem.* 56: 779 (1987)). Monoclonal antibody directed against mammalian RAS proteins immunoprecipitates RAS protein in yeast cells (Powers, S., et al., *Cell* 47: 413 (1986)). Thus, the yeast RAS proteins have the same overall structure and interrelationship as is found in the family of mammalian RAS proteins.

RAS genes have been detected in a wide variety of eukaryotic species, including *Schizosaccharomyces pombe, Dictyostelium discoidem* and *Drosophila melanogaster* (Fukui, Y., and Kaziro, Y., *EMBO* 4: 687 (1985); Reymond, C. D. et al., *Cell* 39: 141 (1984); Shilo, B-Z., and Weinberg, R. A., *Proc. Natl. Acad. Sci., USA* 78: 6789 (1981); Neuman-Silberberg, F., *Cell* 37: 1027 (1984)). The widespread distribution of RAS genes in evolution indicates that studies of RAS in simple eukaryotic organisms may elucidate the normal cellular functions of RAS in mammals.

Extensive genetic analyses of the RAS1 and RAS2 of *S. cerevisiae* have been performed. By constructing in vitro RAS genes disrupted by selectable biochemical markers and introducing these by gene replacement into the RAS chromosomal loci, it has been determined that neither RAS1 nor RAS2 is, by itself, an essential gene. However, doubly RAS deficient (ras1⁻ ras2⁻) spores of doubly heterozygous diploids are incapable of resuming vegetative growth. At least some RAS function is therefore required for viability in *S. cerevisiae* (Kataoka, T., et al., *Cell* 37: 437 (1984)). It has also been determined that RAS1 is located on chromosome XV, 7 cM from ADE2 and 63 cM from HIS3; and that RAS2 is located on chromosome XIV, 2 cM from MET4 (Kataoka, T., et al., *Cell* 37: 437 (1984)).

Mammalian RAS expressed in yeast can function to correct the phenotypic defects that otherwise would result from the loss of both RAS1 and RAS2 (Kataoka, T., et al., *Cell* 40: 19 (1985)). Conversely, yeast RAS are capable of functioning in vertebrate cells (De Feo-Jones, D., et al., *Science* 228: 179 (1985)). Thus, there has been sufficient conservation of structure between yeast and human RAS proteins to allow each to function in heterologous host cells.

The missense mutant, $RAS2^{val19}$, which encodes valine in place of glycine at the nineteenth amino acid position, has the same sort of mutation that is found in some oncogenic mutants of mammalian RAS genes (Tabin, C. J., et al., *Nature* 300: 143 (1982); Reddy, E. P., et al., *Nature* 300: 149 (1982); Taparowsky, E., et al., *Nature* 300: 762 (1982)). Diploid yeast cells that contain this mutation are incapable of sporulating efficiently, even when they contain wild-type RAS alleles (Kataoka, T., et al., *Cell* 37: 437 (1984)). When an activated form of the RAS2 gene (e.g., $RAS2^{val19}$) is present in haploid cells, yeast cells fail to synthesize glycogen, are unable to arrest in G1, die rapidly upon nutrient starvation, and are acutely sensitive to heat shock (Toda, T., et al., *Cell* 40: 27 (1985); Sass, P., et al., *Proc. Natl. Acad. Sci.* 83: 9303 (1986)).

*S. cerevisiae* strains containing $RAS2^{val19}$ have growth and biochemical properties strikingly similar to yeast carrying the IAC or bcy1⁻ mutations, which activate the cAMP pathway in yeast (Uno, I., et al., *J. Biol. Chem.* 257: 14110 (1981)). Yeast strains carrying the IAC mutation have elevated levels of adenylate cyclase activity. bcy1- cells lack the regulatory component of the cAMP dependent protein kinase (Uno, I. et al., *J. Biol. Chem.* 257: 14110 (1982); Toda, T., et al., *Mol. Cell. Biol* 7: 1371 (1987)). Yeast strains deficient in RAS function exhibit properties similar to adenylate cyclase-deficient yeast (Toda, T., et al., *Cell* 40: 27 (1985)). The bcy1⁻ mutation suppresses lethality in ras1⁻ ras2⁻ yeast. These results suggest that in the yeast *S. cerevisiae*, RAS proteins function in the cAMP signalling pathway.

Adenylyl cyclase has been shown to be controlled by RAS proteins (Toda, T., et al., *Cell* 40: 27 (1985)). RAS proteins, either from yeast or humans, can stimulate adenylyl cyclase up to fifty fold in in vitro biochemical assays. RAS proteins will stimulate adenylyl cyclase only when bound with GTP (Field, J., et al., *Mol. Cell. Biol.* 8: 2159 (1988)).

The phenotypes which are due to activation of RAS, including sensitivity to heat shock and starvation, are primarily the result of overexpression or uncontrolled activation of the cAMP effector pathway via adenylyl cyclase (Kataoka, T., et al., *Cell* 37: 437 (1984); Kataoka, T. et al., *Cell* 43: 493 (1985); Toda, T. et al., *Cell* 40: 27 (1985); Field J., et al., *Mol. Cell. Biol.,* 8: 2159 (1988)). Two *S. cerevisiae* yeast genes, PDE1 and PDE2, which encode the low and high affinity cAMP phosphodiesterases, respectively, have been isolated (Sass, P., et al., *Proc. Natl. Acad. Sci.* 83: 9303 (1986); Nikawa, J., et al., *Mol. Cell. Biol.* 7: 3629 (1987)). These genes were cloned from yeast genomic libraries by their ability to suppress the heat shock sensitivity in yeast cells harboring an activated $RAS2^{val19}$ gene. Cells lacking the PDE genes (i.e., pde1⁻ pde2⁻ yeast) are heat shock sensitive, are deficient in glycogen accumulation, fail to grow on an acetate carbon source, and in general have defects due to activation of the cAMP signaling pathway (Nikawa, J., et al., *Mol. Cell. Biol.* 7: 3629 (1987)).

Genetic analysis clearly indicates that RAS proteins have other functions in *S. cerevisiae* besides stimulating adenylyl cyclase (Toda, T. et al., *Japan Sci Soc*. Press. Tokyo/VNU Sci. Press, pp. 253 (1987); Wigler, M. et al., *Cold Spring Harbor Symposium.* Vol. LIII 649 (1988); Michaeli, T., et al., *EMBO* 8: 3039 (1989)). The precise biochemical nature of these functions is unknown. Experiments with other systems, such as *S. pombe* and *Xenopus laevis* oocytes, indicate that RAS stimulation of adenylyl cyclase is not widespread in evolution (Birchmeier, C., et al., *Cell* 43: 615 (1985)). It is unlikely that RAS stimulates adenylyl cyclase in mammals (Beckner, S. K. et al. , *Nature* 317: 71 (1985) Identification of Mammalian Genes. Exemplified by Genes Encoding cAMP Phosphodiesterases The present method can be used to clone a mammalian gene of interest which functions in a microorganism which is genetically altered or defective in a defined manner (an altered microorganism) to correct the genetic alteration or defect and, as a result, modifies an identifiable phenotypic alteration or characteristic associated with the genetic alteration or defect (produces a phenotype more like that of normal or unaltered yeast). Although use of the present method to clone and identify mammalian genes is described in detail in respect to cAMP phosphodiesterases and proteins which interact with RAS proteins, it can be used to clone and identify other mammalian genes which function in an appropriately-selected altered microorganism to correct, complement or supplement the genetic alteration and, as a result, correct the associated phenotypic alteration.

In its most general form, the method of the present invention is represented in FIG. 1 and can be described as follows: A cDNA library of mammalian mRNAs is produced, using known techniques. This library can be made by cloning double stranded cDNA into an expression vector. The cDNA can be prepared from a preexisting cDNA library, or it can be prepared by the reverse transcription of mRNA purified from a tissue or cell line of choice, using standard procedures (Watson, C. J. and Jackson, J. F. In: *DNA cloning, a practical approach*, IRL Press Oxford (1984)). This is described in greater detail in Example 1, in which cDNA was derived from rat brain mRNA and in Example 2, in which the cDNA was derived from a human glioblastoma cell line, U1188MG.

The cDNA obtained is cloned into an expression vector capable of expressing mammalian cDNA inserts as mRNA which can be translated into protein in a host cell of choice. Any expression vector, such as pADNS, into which the cDNA can be inserted and subsequently expressed as mRNA which is translated in an appropriate altered host cell (e.g., altered yeast) can be used. Vectors which have been used for this purpose are described; see FIG. 2A, which is a schematic representation of the expression vector TK161-R2V, whose use is described in Examples 1 and 2, and FIG. 2B, which is a schematic representation of the expression vector pADNS, whose use is described in Example 2. In general, an expression vector contains a transcriptional promoter specific for the host cell into which the vector is introduced. For example, the vector used in Examples 1 and 2 contains promoters for expression in S. cerevisiae. The expressed mRNA may utilize the ATG of the cDNA insert as the "start" codon (e.g., the vector of FIG. 2A) or may express the cDNA product as a fusion protein (e.g., the vector of FIG. 2B).

The cDNA library (present as cDNA inserts in a selected expression vector) is introduced into a host cell of choice, which contains genetic alterations which cause the host cell to have an identifiable phenotypic alteration or abnormality associated with the genetic alteration. The host cell may be a eukaryotic microorganism, such as the yeast S. cerevisiae. Known methods, such as lithium acetate-induced transformation, are used to introduce the cDNA-containing expression vector. The genetic alterations may lead to defects in the metabolic pathways controlled by the RAS proteins and the associated readily discernible phenotype may be sensitivity to heat shock or nitrogen starvation, failure to synthesize normal amounts of glycogen, failure to grow on certain carbon sources, failure to sporulate, failure to mate, or other properties associated with defects in the pathways controlled by RAS proteins. For example, as described in Examples 1 and 2, the genetic alteration can be the presence of the $RAS2^{val19}$ gene. Yeast containing such an alteration exhibit heat shock sensitivity, which, as described in Examples 1 and 2, can be overcome by expression of mammalian genes. Other genetic alterations can be chosen, such as disruptions of the PDE1 and PDE2 genes in S. cerevisiae or disruptions of, or the presence of an activated allele of, ras1 in S. pombe. Different genetic alterations in the host cell may be correctable by different subsets of mammalian cDNA genes.

After introduction of the cDNA insert-containing expression vector, host cells are maintained under conditions appropriate for host cell growth. Those host cells which have been corrected for their phenotypic alteration are selected and the mammalian gene which they express is recovered (e.g., by transformation of E. coli with DNA isolated from the host cell). The mammalian gene is isolated and can be sequenced and used for further analysis in a variety of ways. For example, the encoded protein can be identified and expressed in cultured cells for use in further processes.

The present method has been used, as described in Examples 1 and 2, to isolate new mammalian genes whose presence in yeast cells has resulted in correction of a phenotypic alteration associated with a genetic alteration (the presence of the $RAS2^{val19}$ gene). The nucleotide sequences of these genes, as well as the amino acid sequence encoded by each, are described in Examples 1 and 2, and are shown in FIGS. 3–7. The genes of FIG. 3 and 4 are homologous to the D. melanogaster dunce gene. The gene of FIG. 3 has also been recently isolated by others using the D. melanogaster dunce gene as probe (Swinnen, J. V., et al., Proc. Natl. Acad. Sci. 86: 5325 (1989)).

Screening and Identification of Agents Which Alter cAMP Phosphodiesterase Activity In its most general form, the second part of the invention (pharmacological screening) is carried out as follows: It is possible to screen for agents that reduce or stimulate the activity of any mammalian protein whose presence or expression in an altered microbial host cell in which a genetic alteration is associated with an identifiable phenotypic alteration results in correction of the phenotypic alteration. Two types of screens are possible, and are illustrated in Examples 3 and 4.

The first type of pharmacological screen is applicable when the mammalian gene encodes a protein of known and assayable biochemical function. The mammalian gene is first expressed in a microbial host by utilizing an appropriate host expression vector of the type already described. Extracts of host cells are prepared, using known techniques; the cells are disrupted and their cellular constituents released. Crude cellular extract or purified mammalian protein is assayed for the known biochemical function in the presence of agents, the effects of which on the protein are to be assessed. In this manner, agents which inhibit or stimulate the activity of the mammalian protein can be identified.

This type of procedure can be carried out to analyze the effects of selected agents on mammalian cAMP phosphodiesterases. For example, a yeast strain lacking both endogenous PDE1 and PDE2 genes can be used as the host cell, into which cDNA encoding mammalian cAMP phosphodiesterase is introduced in an appropriate expression vector and expressed. Such a host cell is particularly useful because there is no background cAMP phosphodiesterase activity (Colicelli, J., et al., Proc. Natl. Acad. Sci. USA 86:3599 (1989)) and hence activity of the mammalian enzyme can be cleanly assayed even in crude cell extracts. This procedure is illustrated in Example 3, in which it is demonstrated that the enzymatic activity of the rat DPD gene product is inhibited by the pharmacological agents Rolipram and R020 1724, but not by the pharmacological agent theophylline.

The second type of pharmacological screen is applicable even when the mammalian gene encodes a protein of unknown function, and, thus, cannot be assayed by a biochemical activity. In this method, agents to be tested are applied or introduced directly to the genetically altered microbial host expressing the mammalian protein. Agents capable of inhibiting the mammalian gene or gene product are identified by their ability to reverse the phenotype originally corrected by expression of the mammalian protein in the altered host.

This procedure has been used for mammalian cDNAs encoding cAMP phosphodiesterases and a yeast containing $RAS2^{val19}$ as the host strain (see Example 4). This host is heat shock sensitive. When the rat DPD gene is introduced into the heat shock sensitive host and expressed, the host strain becomes resistant to heat shock. When the now-resistant cells are incubated in Rolipram, they become heat shock sensitive again, indicating that Rolipram inhibits the activity of the rat DPD gene product. This pharmacological screen does not require that the function of the DPD gene product be known. This same approach can be applied to the genes which are the products of Example 2.

Applications of the Present Method and Products

The present method is useful for cloning novel mammalian genes which encode cAMP phosphodiesterases or proteins which interact with a RAS protein. As described, novel mammalian genes have been cloned, using the present method, and the amino acid sequence of the encoded protein has been deduced. Other mammalian genes encoding additional cAMP phosphodiesterases or additional proteins which interact with a RAS protein can be cloned using the method described. All or a portion of the sequence of the mammalian genes encoding cAMP phosphodiesterases can be used as probes, in known techniques, to identify homologs and the products encoded by such assayed homologs as described herein for cAMP phosphodiesterase activity. Similarly, all or a portion of the mammalian genes encoding products which interact with RAS proteins can be used to identify homologs and the ability of the encoded proteins to interact with RAS proteins assessed as described herein.

Alternatively, mammalian genes encoding other proteins which function in an altered microorganism to correct, complement or supplement the altered or defective genetic activity can be cloned, using a microorganism with an appropriately-selected alteration (e.g., a change in a different biochemical pathway) which is associated with an identifiable phenotypic characteristic.

The present invention is also useful for identifying agents, particularly chemical compounds, which alter (reduce or stimulate) cAMP phosphodiesterase and, thus, affect cAMP activity (e.g., by causing more rapid cAMP breakdown or inhibiting cAMP breakdown and, thus, shortening or prolonging the duration of cAMP activity, respectively). The present method is also useful for identifying agents which alter (inhibit or enhance) the interaction of gene products with RAS proteins.

Antibodies specific for proteins encoded by the mammalian genes isolated using the present method can be produced, using known techniques. Such antibodies may be polyclonal or monoclonal and can be used to identify cAMP phosphodiesterases or proteins which interact with RAS proteins (e.g., the same proteins as those encoded by the mammalian genes or proteins sufficiently similar to the encoded proteins that they are recognized or bound by an antibody raised against the encoded proteins).

The present invention will now be illustrated by the following examples, which are not intended to be limiting in any way.

EXAMPLE 1

Figure 2A:
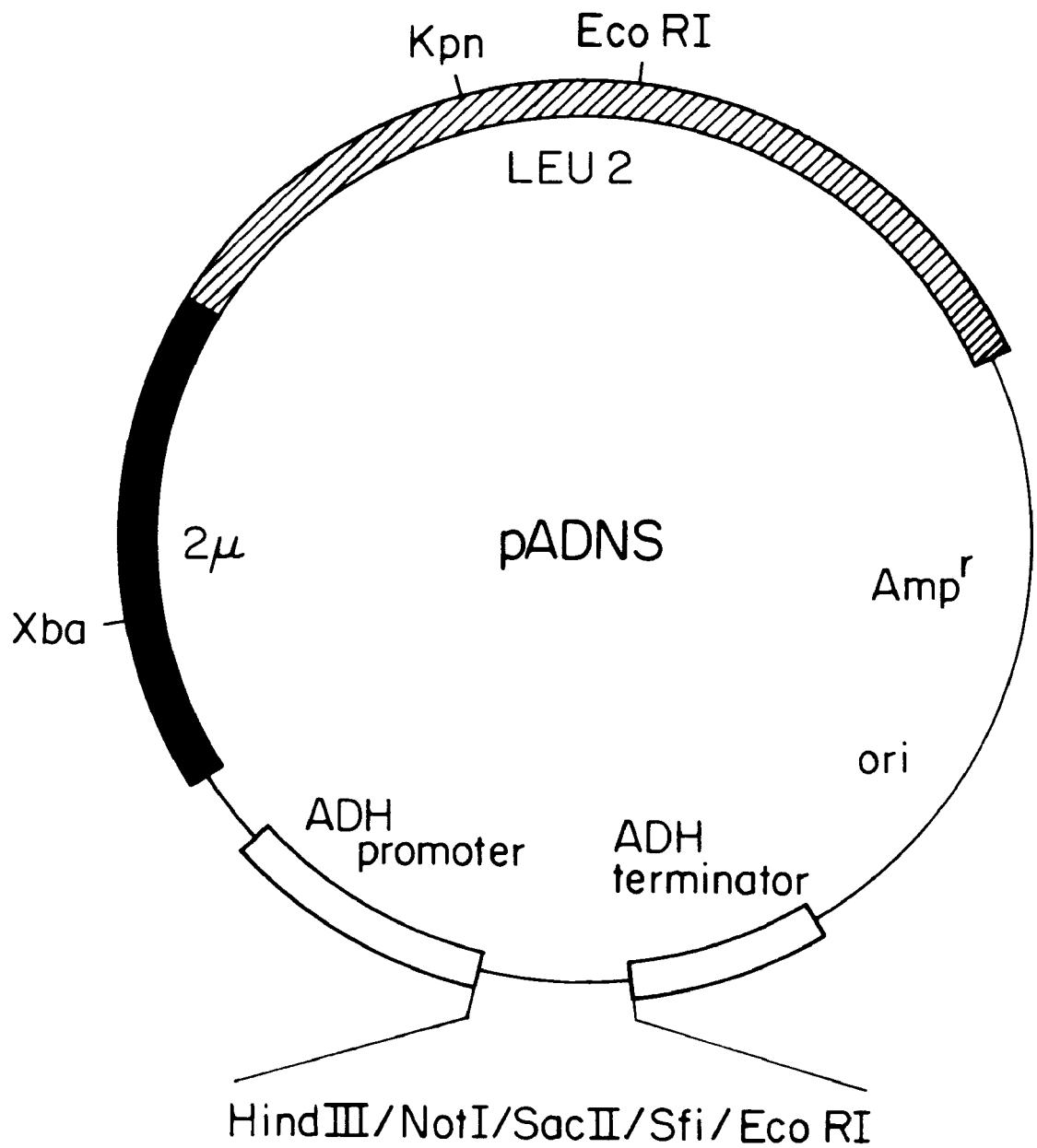
FIG. 2A is a schematic representation of yeast expression vector pADNS.
Figure 2B:
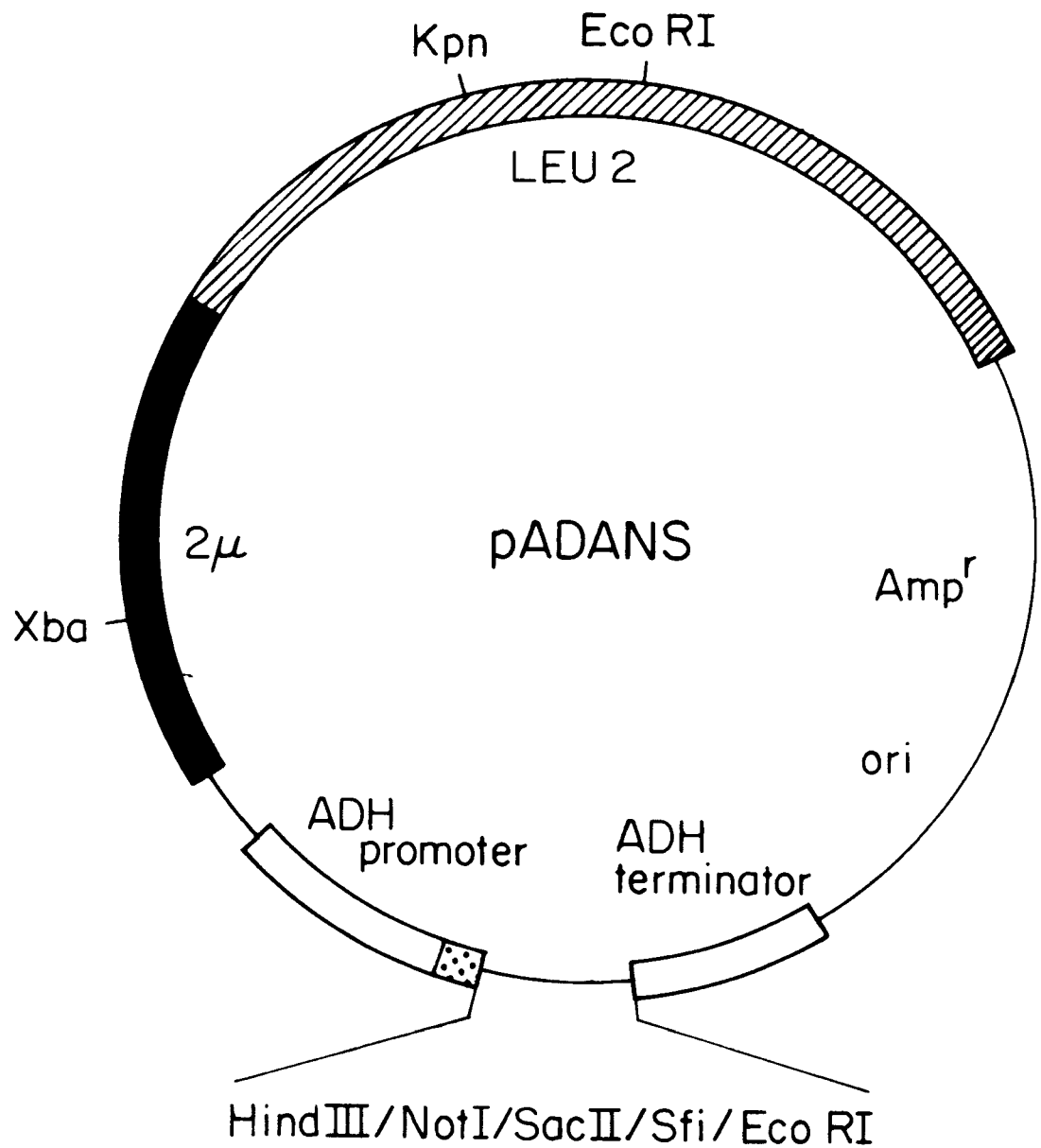
FIG. 2B is a schematic representation of yeast expression vector pADANs. The origins of replication (ori, 2 μ) and selectable markers (AmpR, LEU2) are shown, as are the alcohol dehydrogenase (ADH) promoter and terminator sequences. The polylinker restriction endonuclease sites are as shown.

Identification of a Mammalian Gene That Can Revert the Heat Shock Sensitivity of RAS2$^{val19}$ Yeast Several yeast genes have been isolated which, when overexpressed on extrachromosomal yeast vectors, are capable of suppressing the heat shock sensitivity exhibited by the RAS2$^{val19}$ expressing strain TK161-R2V (Sass, P., et al., *Proc. Natl. Acad. Sci. USA* 83 (1986); Nikawa, J., et al., *Mol. Cell. Biol.*, 7:3629 (1987)). As described in this example, mammalian genes that can function in yeast to render RAS2$^{val19}$ cells resistant to heat shock have now been isolated. A rat brain cDNA library was produced and cloned into the yeast expression vector, pADNS (FIG. 2A). Double stranded cDNAs were prepared and ligated to NotI linkers, cleaved with NotI restriction enzyme, and cloned into pADNS at the NotI site situated between the alcohol dehydrogenase promoter and termination sequences of the vector. The use of the rare cutting NotI obviated the need for restriction site methylases commonly used in cDNA cloning.

Approximately 1.5×10$^5$ independent cDNA inserts were contained in the library, with an average insert size of 1.5 kbp. DNA prepared from the cDNA expression library was used to transform the RAS2$^{val19}$ yeast strain, TK161-R2V. 50,000 Leu$^+$ transformants obtained were subsequently tested for heat shock sensitivity. Only one transformant displayed heat shock resistance which was conditional upon retention of the expression plasmid. A plasmid, pADPD, was isolated from this transformant and the 2.17 kb NotI insert was analyzed by restriction site mapping and nucleotide sequencing (FIG. 2).

A large open reading frame of 562 codons was found. The first ATG appears at codon 46 and a protein which initiates at this codon would have a predicted molecular weight of approximately 60 kDa. This gene is designated DPD. A search for similar sequences was performed by computer analysis of sequence data banks, and the *Drosophila melanogaster* dunce gene was found. The two genes would encode proteins with an 80% amino acid identity, without the introduction of gaps, over a 252 amino acid region located in the center of the rat DPD cDNA. The dunce gene has been shown to encode a high affinity cAMP phosphodiesterase (Chen, C., et al., *Proc. Natl. Acad. Sci. USA* 83:9313 (1986); Davis, R. L. and Kiger, J. A. *J. Cell Biol.* 90:101 (1981); Walter, M. F. and Kiger, J. A. *J. Neurosci.* 4:494 (1984)).

In order to demonstrate that the sequences upstream and downstream of the large sequence identity region were in fact contiguous with that region in the mRNA, rather than artifacts of the method for cDNA cloning, the structure of the cloned cDNA was compared with the structure of DPD cDNAs contained in an independently prepared, first strand cDNA population obtained by reverse transcribing total rat brain poly (A)$^+$ RNA with an oligo dT primer. Oligonucleotide primers complementary to sequences located within the identity region, and to sequences near the 5' or 3' ends of the coding strand, were made. Using either the cloned DPD DNA or the total first strand cDNA material as template, polymerase chain reactions (PCR) were carried out using four different primer sets and the reaction products were analysed by polyacrylamide gel electrophoresis. In each case, a fragment of the predicted length was obtained using either of the template DNAs. The band assignments were confirmed by cleavage with restriction endonucleases having recognition sites within the amplified DNA product. Again, in each case, the primary PCR product obtained using either source of template yielded cleavage products of the predicted sizes. The results indicate that the sequence arrangement in the cloned cDNA faithfully reflects the structure of the rat mRNA.

Expression and Characterization of the DPD Gene Product

*S. cerevisiae* encodes two cAMP phosphodiesterase genes, PDE1 and PDE2 (Sass, P., et al., *Proc. Natl. Acad. Sci. USA* 83:9303 (1986); Nikawa, J., et al., *Mol. Cell. Biol.* 7:3629 (1987)). The *S. cerevisiae* strain 10DAB carries disruptions of both of these genes. The resulting cAMP phosphodiesterase deficiency leads to elevated intracellular cAMP levels and a heat shock sensitivity phenotype similar to that of strains harboring the RAS2$^{val19}$ allele (Nikawa, J., et al., *Mol. Cell. Biol.* 7:3629 (1987). 10DAB cells were transformed with the DPD expression plasmid, pADPD, and assayed for heat shock sensitivity. Expression of the rat DPD gene indeed rendered this host resistant to heat shock.

In order to analyse the biochemical properties of the DPD gene product, crude cell extracts were prepared from one liter cultures of 10DAB which had been transformed with either pADNS or pADPD. Phosphodiesterase activity assays were performed using cAMP as substrate. Control extracts (10DAB with pADNS) showed no cAMP phosphodiesterase activity. Results with the controls were unchanged when performed at 0° C. or in the absence of Mg$^{2+}$ and were comparable to results obtained when no extract was added. These results indicate that there is no detectable background phosphodiesterase activity in strain 10DAB.

In contrast, considerable cAMP phosphodiesterase activity was seen in the 10DAB strain transformed with pADPD. The rate of cAMP hydrolysis in cells containing DPD was measured as a function of cAMP concentration. The deduced Km for cAMP is 3.5 µM and the calculated Vmax is 1.1 nmol/mg/min.

The assay conditions were varied in order to ascertain the cation preferences of the enzyme and to determine the ability of calcium and calmodulin to stimulate its activity. In these assays, Mn$^{2-}$ can be utilized as well as Mg$^{2-}$, and either cation in 1 mM final concentration was sufficient. Calcium/calmodulin was unable to stimulate the measured phosphodiesterase activity in the extract. A parallel assay using beef heart phosphodiesterase (Boeringer Mannheim) yielded a 6.5 fold stimulation with the addition of calcium/calmodulin. Finally, no cGMP phosphodiesterase activity was detected in these assays. Beef heart phosphodiesterase was again used as a positive control. In addition, cGMP present in amounts 100 fold over substrate concentrations was unable to inhibit cAMP phosphodiesterase activity.

Strains, Media, Transformations and Heat Shock

Escherichia coli strain HB101 was used for plasmid propagation and isolation, and strain SCS1 (Stratagene) was used for transformation and maintenance of the cDNA library (Mandel, M., and Higa, A. *J. Mol. Biol.* 53: 159 (1970); Hanahan, D. *J. Mol. Biol.* 166:557 (1983)). *Saccharomyces cerevisiae* strain TK161-R2V (MAT a leu2 his3 ura3 trp1 ade8 can1 RAS2$^{va119}$) (Toda, T., et al., *Cell* 40:27 (1985) and strain 10DAB were used. Strain 10DAB was created from a segregant of a diploid strain produced by mating TS-1 (Kataoka, T., et al., *Cell* 40:19 (1985)) and DJ23-3C (Nikawa, J. I., et al., *Genes and Development* 1:931 (1987)). The segregant (MATα leu2 his3 ura3 ade8 pde1::LEU2 pde2::URA3 ras1::HIS3) was subsequently transformed with the 5.4 kbp Xba1 pde1::ADE8 fragment of pYT19DAB to yield strain 10DAB. Yeast cells were grown in either rich medium (YPD) or synthetic medium with appropriate auxotrophic supplements (SC) (Mortimer, R. K. and Hawthorne, D. C. In: *The Yeast, vol.* 1 385 (1969)). Transformation of yeast cells was performed with lithium acetate (Ito, H., et al., *J. Bacteriol.*, 153:163 (1983)). Heat shock experiments were performed by replica plating onto preheated SC plates which were maintained at 55° C. for 10 minutes, allowed to cool, and incubated at 30° C. for 24–48 hrs. Segregation analysis was performed by growing yeast transformants in YPD for 2–3 days, plating onto YPD plates, and replica plating onto YPD, SC-leucine (plasmid selection), and YPD heat shock plates.

Plasmids, DNA Manipulations and Sequencing

Plasmid DNA from individual *E. coli* colonies was purified by standard procedures (Holmes, D. S., and Quigley, M. *Anal. Biochem* 114 193 (1981); Katz, L., et al., *J. Bacteriol.* 114 477 (1973). Extrachromosomal DNA was isolated from yeast as previously described (Nikawa, J. et al., *Mol. Cell. Biol.*, 7:3629 (1987)). The plasmid pYT19DAB was constructed from pYT19 (Nikawa, J. et al., *Mol. Cell. Biol.*, 7:3629 (1987)) by first deleting PDE1 sequences between the SmaI and BalI restriction sites to yield pYT19D. The 4 kbp BamHI fragment of the ADE8 gene was then inserted into the BamHI site of pYT19D to yield pTY19DAB. The cloning vector pADNS is based on the plasmid pAD1 previously described (Powers, S., et al., *Cell* 47:413 (1986)). pADNS consists of a 2.2 kbp BglII to HpaI fragment containing the *S. cerevisiae* LEU2 gene from YEp213 (Sherman, F., Fink, et al., *Laboratory Course Manual for Methods in Yeast Genetics*, eds. Sherman, F., Fink, G. R. and Hicks, J. B., Cold Spring Harbor Laboratory, Cold Spring Harbor, N.Y. (1986)), a 1.6 kbp HpaI to HindIII fragment of the *S. cerevisiae* 2 μ plasmid containing the origin of replication, and a 2.1 kbp SspI to EcoRI fragment containing the ampicillin resistance gene from the plasmid pUC18. It also contains a 1.5 kbp BamHI to HindIII fragment of the modified *S. cerevisiae* alcohol dehydrogenase (ADH1J) promoter (Bennetzen, J. L. and Hall. B. D. *J. Biol. Chem.* 257:3018 (1982); Ammerer, G. *Meth. Enzymol.* 101:192 (1983)) and a 0.6 kbp HindIII to BamHI fragment containing the ADH1 terminator sequences. The promoter and terminator sequences are separated by a polylinker that contains the restriction endonuclease sites NotI, SacII, and SfiI between the existing HindIII and SacI sites. The oligonucleotides used to create these sites were 5'-GGCCAAAAAGGCCGCGGCCGCA and 5'-TCGACCGGTTTTTCCGGCGCCGGCGTTCGA. The plasmid pADPD is a pADNS-derived plasmid containing the 2.17 kbp DPD cDNA insert.

Sequencing was performed using the dideoxy chain termination method (Sanger, R., et al., *Proc. Natl. Acad. Sci. USA* 74:5463 (1977); Biggin, M. D., et al., *Proc. Natl. Acad. Sci. USA* 80:3963 (1983)). Genalign was used to align the DPD and dunce sequences (GENALIGN is a copyrighted software product of IntelliGenetics, Inc.; developed by Dr. Hugo Martinez). RNA was purified from Sprague-Dawley rat brains by published procedures (Chirgwin, J. M. et al., *Biochem.* 18:5294 (1979); Lizardi, P. M. *Methods Enzymol* 96:24 (1983); Watson C. J. and Jackson J. F. In: *DNA cloning, a practical approach*, IRL Press Oxford (1984)). cDNAs were ligated to the NotI linker oligonucleotides 5'-AAGCGGCCGC and 5'-GCGGCCGCTT. The cDNAs were cleaved with NotI and cloned into the NotI site of pADNS using standard procedures.

Polymerase chain reactions (PCRs) were carried out in thermocycler (Perkin Elmer, Cetus) using a modification of published procedures (Saiki, R., et al., *Science* 239:487 (1988)). Reaction mixtures contained template DNA (1 ng of cloned DNA, or 1 μg of total first strand cDNA), 25 pmoles of oligonucleotide primers, 200 μM deoxyribonucleotide triphosphates, 10 mM Tris HCl (Ph8.4), 50 mM KCl, 3 mM MgCl$_2$, and 0.01% (w/v) gelatin. The oligonucleotide primers used, as designated in FIG. 4, were:

A, 5'-CACCCTGCTGACAAACCT$^{44}$;
B, 5'-ATGGAGACGCTGGAGGAA$^{153}$;
C, 5'-ATACGCCACATCAGAATG$^{676}$;
D, 5'-TACCAGAGTATGATTCCC$^{1449}$;
E, 5'-GTGTCGATCAGAGACTTG$^{1668}$ and
F, 5'-GCACACAGGTTGGCAGAC$^{2048}$.

The numbers indicate position coordinates in FIG. 3. Primers C, E and F are non-coding strand sequences. Thirty cycles (1.5 min at 94° C., 3 min at 55° C., and 7 min at 72° C.) were performed and the reaction products were analysed by polyacrylamide gel electrophoresis.

Phosphodiesterase Assays

Yeast cells were grown at 30° C. for 36 hours in one liter cultures of synthetic media (SC-leucine). Cells were harvested and washed with buffer C (20 mM MES, 0.1 mM MgCl$_2$, 0.1 mM EGTA, 1 mM β-mercaptoethanol), were resuspended in 30 ml buffer C with 50 μl 1M PMSF, and were disrupted with a French press. The extracts were centrifuged at 1,600 g for 10 min and the supernatants were spun at 18,000 g for 90 min (4° C.). The supernatant was assayed for phosphodiesterase activity (Sass, P., et al., *Proc. Natl. Acad. Sci. USA* 83:9303 (1986); Nikawa, J., et al., *Mol. Cell. Biol.* 7:3629 (1987)). All the reactions contained Tris-HCl (pH7.5) (100 mM), cell extract (50 μg protein/ml), 5'-nucleotidase (Sigma, 20 ng/ml) and 10 MM Mg$^{2+}$ (unless otherwise stated) and the indicated cyclic nucleotide concentrations. Assays for the cGMP hydrolysis used 1.5 μM cGMP. Inhibition studies employed 5 μM cAMP in the presence of varying amounts of cGMP up to 500 μM. [$^3$H] cAMP and [$^3$H] cGMP were obtained from NEN (New England Nuclear). Reactions were incubated for 10 min at 30° C. and stopped with 5x stop solution (250 mM EDTA, 25 mM AMP, 100 mMcAMP).

Discussion

Previous workers have cloned a mammalian gene in yeast using a biological screen (Lee, M. G. and Nurse, P. *Nature*

327:31 (1987)). In that case, a homolog to the cdc2 gene of S. pombe was cloned by screening a cDNA library for complementation of cdc2 mutants. In that library, the cDNAs were inserted proximal to the SV40 early T antigen promoter. In our work we have employed a library with mammalian cDNAs inserted into a yeast expression vector, proximal to a strong yeast promoter. In addition, we have employed NotI linkers for cDNA cloning, which allows the convenient subcloning of an entire insert library from one vector to another. We feel that this will be a generally useful approach for cloning genes from higher eukaryotes when functional screens are possible in yeast. This system is particularly useful for the cloning of other cAMP phosphodiesterases from mammals. The availability of yeast strains totally lacking endogenous cAMP phosphodiesterase activity will also facilitate the biochemical characterization of these new phosphodiesterases.

The mammalian DPD cDNA can encode a protein with a high degree of amino acid sequence identity (80%) with the predicted D. melanogaster dunce gene product over an extended region. The dunce gene has been shown to encode a high affinity cAMP phosphodiesterase required for normal learning and memory in flies (Chen, C., et al., Proc. Natl. Acad. Sci. USA 83:9313 (1986); Davis R. L. and Kiger, J. A. J. Cell Biol. 90:101 (1981); Walter, M. F. and Kiger, J. A. J. Neurosci. 4:495 (1984)). Compared to the striking level of sequence identity between DPD and dunce, the sequence conservation among other known cAMP phosphodiesterases is scant (Charbonneau, H., et al., Proc. Natl. Acad. Sci. USA 83:9308 (1986)). Therefore the DPD-dunce homology in the conserved region represents more than a constraint on sequences required for cAMP binding and hydrolysis, and suggests a conservation of interactions with other components.

Biochemical characterization of the DPD cDNA product expressed in yeast indicates that it is a high affinity cAMP specific phosphodiesterase, as is dunce (Davis, R. L. and Kiger, J. A. J. Cell. Biol. 90:101 (1981); Walter M. F. and Kiger, J. A. J. Neurosci. 4 (1984)). In addition, DPD activity, as measured in our assays, is not stimulated by the presence of calcium/calmodulin. This property is shared with dunce and is distinct from some other phosphodiesterases (Beavo, J. A. In Advances in second messenger and phosphorprotein research, eds. Greengard, P. and Robinson, G. A., Raven Press, NY vol. 22 (1988)). The two proteins, DPD and dunce, thus appear to have similar biochemical characteristics. However, it should also be noted that DPD encodes a protein product which shows much less significant homology (35%) to dunce beyond the previously described highly conserved core region. These non-conserved sequences could result in an altered or refined function for this mammalian dunce homolog.

The DPD sequence encodes a methionine codon at position 46 and the established reading frame remains open through to position 563, resulting in a protein with a predicted molecular weight of 60 kDa. The same reading frame, however, is open beyond the 5' end of the coding strand (FIG. 2). At present, it is not known if the methionine codon at position 46 is the initiating condon for the DPD protein. The coding sequence is interrupted by three closely spaced terminator codons. However, the established reading frame then remains open for an additional 116 codons, followed by more terminator codons, a polyadenylation consensus signal and a polyadenine stretch. This 3' open reading frame could be incorporated into another dunce-like phosphodiesterase through alternate splicing.

Davis et al., (Davis, R. L. et al., Proc. Natl. Acad. Sci. USA 86:3604 (1989)) have also isolated a mammalian dunce homolog from a rat brain cDNA library using standard nucleic acid hybridization techniques. The gene which they describe is indeed similar to, through distinct from, the DPD cDNA described here. Within the highly conserved region, as defined in this work, the predicted amino acid sequences of the two rat genes are 93% identical. This homology falls off dramatically, however, in the flanking regions which show amino acid identities of 60% (upstream) and 30% (downstream) and require the use of sequence gaps for optimum alignment.

EXAMPLE 2

Identification of a Human Gene That Can Revert the Heat Shock Sensitivity of $RAS2^{val119}$ Yeast A cDNA library was constructed in λZAP using NotI linkers. In this example, the cDNA derived from mRNA purified from the human glioblastoma cell line U118MG. Inserts from the λ vector were transferred into two yeast expression vectors. One, pADNS, is as described before. The other, pADANS (see FIG. 2B), differs in that the mRNA expressed will direct the synthesis of a fusion protein: an N terminal portion derived from the alcohol dehydrogenase protein and the remainder from the mammalian cDNA insert. Thus, two mammalian cDNA expression libraries were constructed.

These libraries were screened, as in the previous example, for cDNAs capable of correcting the heat shock sensitivity of the S. cerevisiae host TK161-R2V. Several cDNAs were isolated and analysed by sequencing. Four different cDNA genes were thereby discovered, and their sequences are shown in FIGS. 4–7.

The gene of FIG. 4 (JC44) was shown by computer analysis to be homologous to the rat DPD gene. Biochemical analysis has proven that JC44 encodes a cAMP phosphodiesterase. The other genes, called JC99, JC265, and JC310, show no significant homology to previously isolated genes.

The genes of FIGS. 3 and 4 were shown to be able to correct the phenotypic defects of pde1⁻ pde2⁻ yeast strains. The genes of FIGS. 5–7 were unable to do so. Thus, it appears that the latter genes do not encode cAMP phosphodiesterases. Rather, these genes encode proteins of unknown function which appear to be able to correct phenotypic defects in yeast with activated RAS proteins.

Materials and Methods

Procedures of Example 1 were followed throughout. Described here is the construction of the plasmid pADANS, shown in FIG. 2B. A PCR reaction was carried out on the yeast ADH1 gene in pJD14 (Bennetzen, J. L. and Hall, B. D. J. Biol. Chem. 257:2018 (1982)). One oligonucleotide primer (5' TCTAAACCGTGGAATATT) was placed within the promoter region of the gene. The second primer (5'GTCAAAGCTTCGTAGAAGATAACACC) was designed to hybridize within the coding region of the gene. This primer included 5' non-hybridizing sequence encoding a HindIII endonuclease recognition site. The PCR product was then purified, digested with HindIII and EcoRV and ligated into the 8.0 kb HindIII and EcoRV (partial) digested fragment of pADNS. The resulting plasmid, pADANS, contains the entire ADH1 promoter and the first 14 amino acid codons of the ADH1 gene followed by the HindIII and NotI restriction endonuclease sites.

EXAMPLE 3

Identification of Agents Which Inhibit Phosphodiesterase Activity

This example illustrates the use of the genes and cells described in Example 1 to identify chemical compounds which inhibit the activity of a known enzyme, the rat DPD phosphodiesterase. To test the efficiency of known inhibitory compounds, cell free extracts were made as described in Phosphodiesterase Assays. Yeast cells deficient in endogenous phosphodiesterase (10DAB), and expressing the rat DPD or yeast PDE2 genes from the described expression vector, were used. One liter cultures were harvested, washed in buffer C (20 mM MES/0.1 mM $MgCl_2$/0.1 mM EGTA/1 mM 2-mercaptoethanol), resuspended in buffer C containing 1.5 mM phenylmethylsulfonyl fluoride, and disrupted in a French press at 4° C. Cell extracts were clarified at 100 g for 10 minutes and at 18000 g for 90 minutes. PDE activities were assayed as published (Saiki et al., Science 239:487–491 (1988); Charbonneau et al., Proc. Natl. Acad. Sci. USA 83:9308–9312 (1986); Tempel et al., Proc. Natl. Acad. Sci. USA 80:1482–1486 (1983)) in a reaction mix containing 50 µg of cell protein/ml, 100 mM Tris (pH 7.5), 10 mM $Mg^{++}$, 5 µM cAMP, 5'-nucleotidase and [$^3$H] cAMP. Hydrolysed AMP was separated from cAMP using AG1-X8 resin from Bio Rad. About $10^4$ cpm were obtained for 10 minutes reactions and backgrounds (phosphodiesterase deficient-yeast or no extract) were about 300 cpm. The cytosolic fraction was assayed in the presence or absence of inhibitory compounds. These assays measure the amount of adenosine 5' monophosphate (AMP) produced by phosphodiesterase-catalysed hydrolysis of adenosine 3', 5'-cyclic adenosine monophosphate (cAMP). For each extract the percent inhibition for various concentrations of known inhibitors is given in Table 1. The percent inhibition represents the decrease in phosphodiesterase activity relative to measurements made in the absence of inhibitors. Rolipram, and the related compound RO20 1724, were the most effective inhibitors of DPD activity.

TABLE 1

Inhibition of Phosphodiesterases by Chemicals

| Phosphodiesterase | Agent | Concentration (µM) | Inhibition (%) |
| --- | --- | --- | --- |
| PDE2 | Theophylline | 250 | 0.0 |
|  | IBMX | 250 | 0.0 |
|  | RO20 1724 | 100 | 3.0 |
|  | Rolipram | 100 | 0.0 |
| DPD-1 | Theophylline | 250 | 42. |
|  | RBMX | 250 | 87. |
|  | RO20 1724 | 0.1 | 35. |
|  |  | 1.0 | 52. |
|  |  | 10.0 | 79. |
|  |  | 100.0 | 92. |
|  | Rolipram | 0.1 | 50. |
|  |  | 1.0 | 72. |
|  |  | 10.0 | 92. |
|  |  | 100.0 | 95. |

This analysis can, of course, be extended to test new or related chemical compounds for their ability to inhibit DPD activity, or the activity of another phosphodiesterase expressed in this system. Clearly, this form of analysis can also be extended to other genes cloned and expressed in a similar manner, for which there is an assayable enzymatic activity.

EXAMPLE 4

Figure 8:
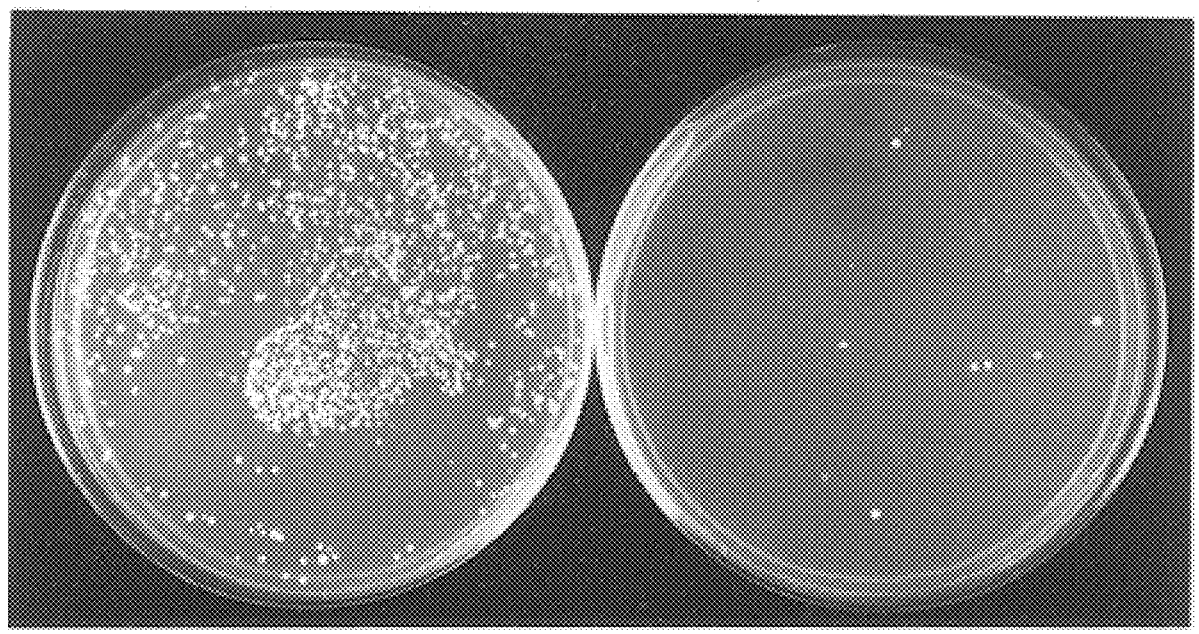
FIG. 8 shows suppression of heat shock resistance resulting from treatment of yeast cultures with a pharmacological agent. Cells on the right plate were pre-treated with 100 μM rolipram prior to heat shock treatment.

Identification of Agents Which Inhibit Mammalian Proteins of Unknown Function Expressed in Yeast This example illustrates the use of the genes and methods described to identify chemical compounds which inhibit the function of the encoded mammalian proteins expressed in yeast, even when the function of that protein is not known. 10DAB cells, which are phosphodiesterase deficient, are sensitive to heat shock. As already discussed, when these cells express DPD, they become resistant to heat shock. FIG. 8 demonstrates the inhibition of DPD function in yeast cells assayed by heat shock survival. 10DAB cells expressing DPD were maintained in rich medium (YPD) for three days at stationary phase. These cultures were then treated with rolipram, a known phosphodiesterase inhibitor, for 40 minutes at a final concentration of 100 µM. Control cultures were not treated with any inhibitor. These cultures were then heat shocked in glass tubes at 50° C. for 30 minutes. One microliter of each culture was plated. As shown in FIG. 8, cultures treated with rolipram (right side) were much more sensitive to heat shock, reflecting an inhibition of DPD enzymatic function.

Similarly, the suppression of heat shock sensitivity in the $RAS2^{val19}$ yeast strain (TK161-R2V) by DPD expression will also be inhibited by drug treatment. In addition, any other phenotype which is dependent on DPD phosphodiesterase activity should be affected by the presence of the inhibitory drug. The effect of a drug or agent can be assessed as described. Finally, in the most generalized case, inhibitory chemicals for proteins of unknown function, expressed from mammalian cDNAs in yeast, can be discovered in a similar way. This approach depends only on the phenotype consequent to expression of the protein and not on knowledge of its function.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of identifying a chemical agent which inhibits a mammalian gene which, when expressed in a genetically altered microorganism, modifies a phenotypic alteration associated with a genetic alteration in the microorganism, comprising the steps of:

a) expressing the mammalian gene in a genetically altered microorganism, thereby modifying the phenotypic alteration associated with the genetic alteration;

b) contacting the genetically altered microorganism of step (a) with a chemical agent to be assayed, under conditions appropriate for phenotypic assay; and c) determining whether the phenotypic alteration associated with the genetic alteration modified in step (a) is reversed, wherein reversal of the phenotypic alteration is indicative of a chemical agent which inhibits the mammalian gene.

2. A method of identifying a chemical agent which inhibits a mammalian gene which, when expressed in genetically altered yeast cells, modifies a phenotypic alteration associated with a genetic alteration in the yeast cells, comprising the steps of:

a) expressing the mammalian gene in genetically altered yeast cells in which the product encoded by the mammalian gene is not expressed, thereby modifying the phenotypic alteration associated with the genetic alteration;

b) contacting genetically altered yeast cells of step (a) with a chemical agent to be assayed, under conditions appropriate for phenotypic assay; and c) determining whether the phenotypic alteration associated with the genetic alteration modified in step (a) is reversed, wherein reversal of the phenotypic alteration is indicative of a chemical agent which inhibits the mammalian gene.

3. The method of claim 2 wherein the genetically altered yeast cells are genetically altered *S. cerevisiae* or genetically altered *S. pombe*.

4. A method of identifying a chemical agent which inhibits a mammalian gene which, when expressed in genetically altered yeast cells, modifies a phenotypic alteration associated with a genetic alternation in the yeast cells said genetic alteration being associated with activation or attenuation of a biochemical pathway in which cAMP participates, comprising the steps of:

a) expressing the mammalian gene in genetically altered yeast cells in which the product encoded by the mammalian gene is not expressed, thereby modifying the phenotypic alteration associated with the genetic alteration;

b) contacting the genetically altered yeast cells of step (a) with a chemical agent to be assayed, under conditions appropriate for phenotypic assay; and c) determining whether the phenotypic alteration associated with the genetic alteration modified in step (a) is reversed, wherein reversal of the phenotypic alteration is indicative of a chemical agent which inhibits the mammalian gene.

5. The method of claim 4 wherein the genetic alteration is a disruption of the PDE1 and a disruption of the PDE2 genes of *S. cerevisiae*.

6. A method of identifying a chemical agent which inhibits a mammalian gene which, when expressed in genetically altered yeast cells, modifies a phenotypic alteration associated with a genetic alteration in the yeast cells said genetic alteration being a mutation in a gene encoding a RAS protein, comprising the steps of:

a) expressing the mammalian gene in genetically altered yeast cells in which the product encoded by the mammalian gene is not expressed, thereby modifying the phenotypic alteration associated with the genetic alteration;

b) contacting the genetically altered yeast cells of step (a) with a chemical agent to be assayed under conditions appropriate for phenotypic assay; and c) determining whether the phenotypic alteration associated with the genetic alteration modified in step (a) is reversed, wherein reversal of the phenotypic alteration is indicative of a chemical agent which inhibits the mammalian gene.

7. The method of claim 6, wherein the genetic alteration is an activated $RAS2^{val119}$ gene of *S. cerevisiae*.

8. The method of claim 6 wherein the genetic alteration is a disruption of the ras1 gene of *S. pombe* or an activated allele of the ras1 gene of *S. pombe*.

9. The method of claim 3 wherein the phenotypic alteration associated with a genetic alteration is selected from the group consisting of: heat shock sensitivity, nitrogen starvation, failure to synthesize normal amounts of glycogen, failure to grow on acetate, failure to mate and failure to sporulate.

10. A method of identifying a chemical agent which alters activity of a protein encoded by a mammalian gene which, when expressed in genetically altered yeast cells, modifies a phenotypic alteration associated with a genetic alteration in the yeast cells, comprising the steps of:

a) expressing the protein encoded by the mammalian gene in genetically altered yeast cells in which the protein encoded by the mammalian gene is not expressed, thereby modifying the phenotypic alteration associated with the genetic alteration;

b) obtaining from genetically altered yeast cells produced in step (a) protein encoded by the mammalian gene;

c) combining protein encoded by the mammalian gene with a chemical agent to be assayed for its ability to alter activity of the protein encoded by the mammalian gene; and d) determining activity of the protein encoded by the mammalian gene in combination with the chemical agent.

* * * * *

UNITED STATES PATENT AND TRADEMARK OFFICE
CERTIFICATE OF CORRECTION

PATENT NO. : 6,080,540
DATED : June 27, 2000
INVENTOR(S) : Wigler et al.

It is certified that error appears in the above-identified patent and that said Letters Patent is hereby corrected as shown below:

Title page,
Column 2,
Line 1, replace "Bil." with -- Biol. --.
Line 7, replace "Acda" with -- Acad. --.
Under address of Assignee, replace "Cold Spring, New York" with -- Cold Spring Harbor, New York --.

Column 1,
Line 8, after "National Institutes of Health" and before the period, insert -- under Grant No. CA39829. The United States government may own certain rights in the invention --.

Column 13,
Line 15, replace "(MAT a leu2" with -- (MAT α leu2 --.
Line 57, replace "2 μ" with -- 2μ --.

Column 15,
Line 58, replace "condon" with -- codon --.

Column 16,
Line 3, replace "through" with -- though --.

Signed and Sealed this

Twenty-fifth Day of December, 2001

Attest:

*Attesting Officer*

JAMES E. ROGAN
*Director of the United States Patent and Trademark Office*